United States Patent
Murphy et al.

(10) Patent No.: US 12,252,556 B2
(45) Date of Patent: Mar. 18, 2025

(54) CYCLOSPORINE COMPOSITIONS AND METHODS OF USE

(71) Applicant: Bacainn Biotherapeutics, Ltd., George Town, KY (US)

(72) Inventors: Chris Murphy, Upton, MA (US); Ronald Farquhar, Boston, MA (US); Roland E. Dolle, Eureka, MO (US)

(73) Assignee: BACAINN BIOTHERAPEUTICS, LTD., George Town (KY)

( * ) Notice: Subject to any disclaimer, the term of this patent is extended or adjusted under 35 U.S.C. 154(b) by 0 days.

(21) Appl. No.: 17/269,614

(22) PCT Filed: Aug. 20, 2019

(86) PCT No.: PCT/US2019/047354
§ 371 (c)(1),
(2) Date: Feb. 19, 2021

(87) PCT Pub. No.: WO2020/041378
PCT Pub. Date: Feb. 27, 2020

(65) Prior Publication Data
US 2021/0277064 A1 Sep. 9, 2021

Related U.S. Application Data

(60) Provisional application No. 62/721,195, filed on Aug. 22, 2018.

(51) Int. Cl.
| C07K 7/64 | (2006.01) |
| A61K 45/06 | (2006.01) |
| A61K 47/60 | (2017.01) |

(52) U.S. Cl.
CPC .............. C07K 7/645 (2013.01); A61K 45/06 (2013.01); A61K 47/60 (2017.08)

(58) Field of Classification Search
None
See application file for complete search history.

(56) References Cited

U.S. PATENT DOCUMENTS

| 2012/0196749 A1* | 8/2012 | Fischer | A61P 29/00 435/375 |
| 2014/0256651 A1 | 9/2014 | Sinha et al. | |
| 2015/0150987 A1 | 6/2015 | Gaudriault et al. | |
| 2016/0166635 A1 | 6/2016 | Coulter | |
| 2016/0207961 A1 | 7/2016 | Hegmans et al. | |
| 2018/0105558 A1 | 4/2018 | Su et al. | |

FOREIGN PATENT DOCUMENTS

| JP | 2011-529451 A | | 12/2011 |
| JP | 2016-539108 A | | 12/2016 |
| WO | WO 97/33604 | * | 9/1997 |
| WO | WO-97/33604 A1 | | 9/1997 |
| WO | WO-98/07713 A1 | | 2/1998 |
| WO | WO-01/05819 A1 | | 1/2001 |
| WO | WO-2010/012073 A1 | | 2/2010 |
| WO | WO-2015/067762 A1 | | 5/2015 |

OTHER PUBLICATIONS

Hadidi et al. (AAPS Pharm Sci Tech, vol. 14, No. 2, Jun. 2013) (Year: 2013).*
Mass General Brigham, downloaded from URL:<https://www.massgeneralbrigham.org/en/about/newsroom/articles/prevent-inflammatory-bowel-disease#:~:text=IBD%20prevention%20and%20risk%20factors,Genetics> (Year: 2024).*
Mayo clinic (downloaded from URL:<https://www.mayoclinic.org/diseases-conditions/asthma/symptoms-causes/syc-20369653#:~:text=Prevention,and%20managing%20an%20asthma%20attack>) (Year: 2024).*
Cleveland clinic (downloaded from URL:<https://my.clevelandclinic.org/health/diseases/12174-rosacea>) (Year: 2024).*
American optometric association (downloaded from URL:<https://www.aoa.org/healthy-eyes/eye-and-vision-conditions/anterior-uveitis?sso=y >) (Year: 2024).*
International Search Report and Written Opinion in International Patent Application No. PCT/US2019/047354 dated Dec. 3, 2019.
Lazarova, et al. "Cyclosporin A analogues: recent advances." Expert Opinion on Therapeutic Patents. Sep. 1, 2003, vol. 13, No. 9, pp. 1327-1332.

* cited by examiner

Primary Examiner — Sergio Coffa
(74) Attorney, Agent, or Firm — FOLEY & LARDNER LLP

(57) ABSTRACT

Disclosed herein are cyclosporine compounds and methods for use in the treatment or prevention of neutrophil-mediated inflammation, wherein the compounds inhibit the activity of MRP2 and FPR1.

23 Claims, 6 Drawing Sheets

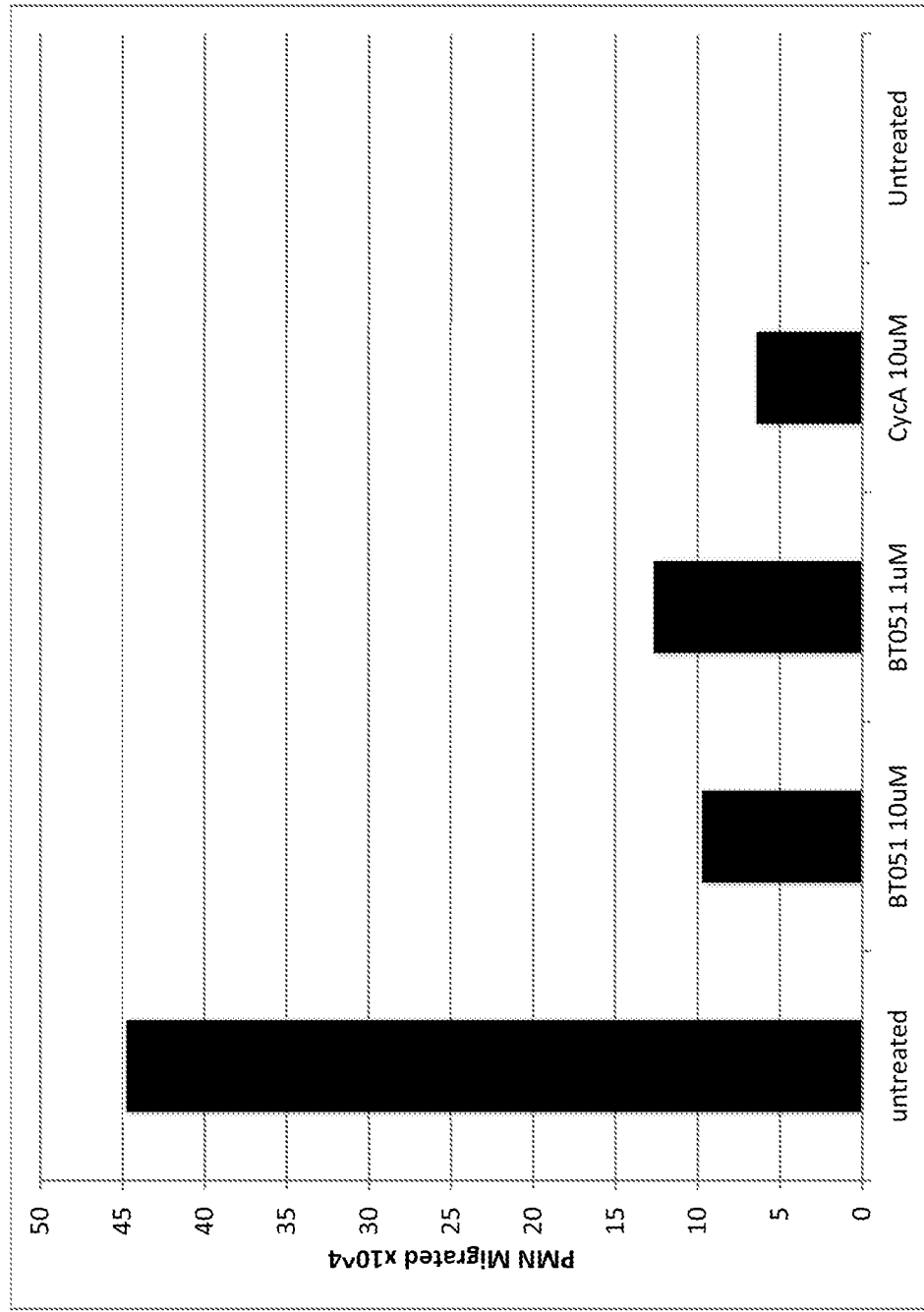

CYCLOSPORINE COMPOSITIONS AND METHODS OF USE

CROSS-REFERENCE TO RELATED APPLICATION

The present application is a U.S. National Phase Application under 35 U.S.C. § 371 of International Application No. PCT/US2019/047354, filed on Aug. 20, 2019, which claims priority to U.S. Provisional Patent Application No. 62/721,195, filed on Aug. 22, 2018, the contents of which are hereby incorporated by reference in their entireties.

TECHNICAL FIELD

The technology of the present disclosure relates to methods, compounds, and compositions for treating or preventing disease associated with neutrophil-mediated inflammation.

BACKGROUND

Inflammation, and in particular chronic inflammatory disease (CID), is globally highly prevalent and is viewed as one of the major causes for the development of different diseases like cardiovascular disease, diabetes, obesity, osteoporosis, rheumatoid arthritis, inflammatory bowel disease, asthma, and CNS related diseases such as depression and Parkinson's disease. Epithelial cells dramatically increase surface expression of the membrane ABC transporter multidrug resistance protein 2 (MRP2) in response to infection with *Salmonella enterica* serovar *Typhimurium* (*Salmonella typhimurium*) or a variety of other pathogens. The intracellular biosynthetic pathway of the eicosanoid $HXA_3$ is concurrently upregulated, and increased MRP2 at the surface serves to transport $HXA_3$ into the intestinal lumen. This establishes a concentration gradient of $HXA_3$ across the epithelium that directs chemotaxis of neutrophils from the basolateral side into the lumen, resulting in a critical inflammatory process. Hence, inhibition of MRP2 is an avenue for the treatment or prevention of inflammatory disease.

Gluten-containing cereals, e.g., wheat, rye and barley, are an important part of the human diet. However, gliadin, the main component of gluten, has been implicated in a variety of disorders including celiac disease, irritable bowel syndrome, non-celiac gluten sensitivity, type 1 diabetes, schizophrenia, and autism. It has been shown that gliadin increases gut epithelial permeability, and acts as a neutrophil chemoattractant factor of similar potency to fMet-Leu-Phe through binding to FPR1. Hence, inhibition of FPR1 is an avenue for the treatment or prevention of gliadin-related conditions.

SUMMARY

In one aspect, the present disclosure relates to a compound having the structure of Formula I,

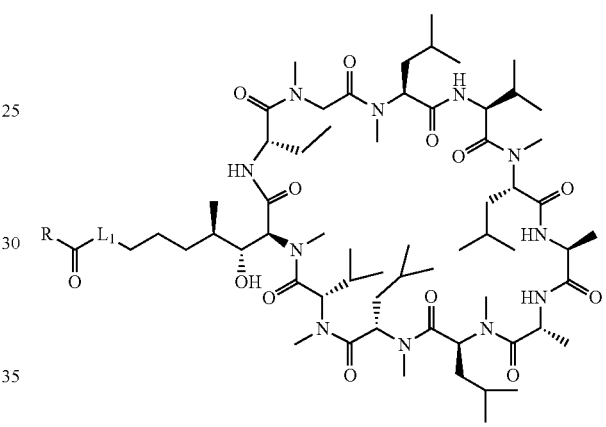

(I)

a stereoisomer thereof, or a pharmaceutically acceptable salt of any of the foregoing; wherein $L_1$ is a $C_0$ to $C_4$ alkyl group optionally substituted with one or more F; R is selected from the group consisting of —OH and a PEG, wherein the PEG optionally comprises a linker group, $L_2$.

In some embodiments, R is selected from —OH or —NH(CH$_2$)$_{2-6}$(CH$_2$CH$_2$O)$_{42-46}$—O(CH$_2$)$_{0-5}$CH$_3$. In some embodiments, R is selected from the group consisting of CH$_3$O—(CH$_2$CH$_2$O)$_{44}$—CH$_2$CH$_2$CH$_2$NH— (BT051), CH$_3$O—(CH$_2$CH$_2$O)$_{44}$—CH$_2$CH$_2$NH— (BT090), and HO— (BT070).

In some embodiments, $L_1$ is an ethylene group or a propylene group.

In some embodiments, R is a PEG having from 40 to 50 ethylene oxide units.

In some embodiments, $L_2$ is a substituted or unsubstituted heteroalkylene group.

In some embodiments, $L_2$ is a $C_{1-6}$ unsubstituted heteroalkylene having one or two nitrogen atoms.

In some embodiments, the compound has the structure of Formula IA, a stereoisomer thereof, or a pharmaceutically acceptable salt of any of the foregoing:

(IA)

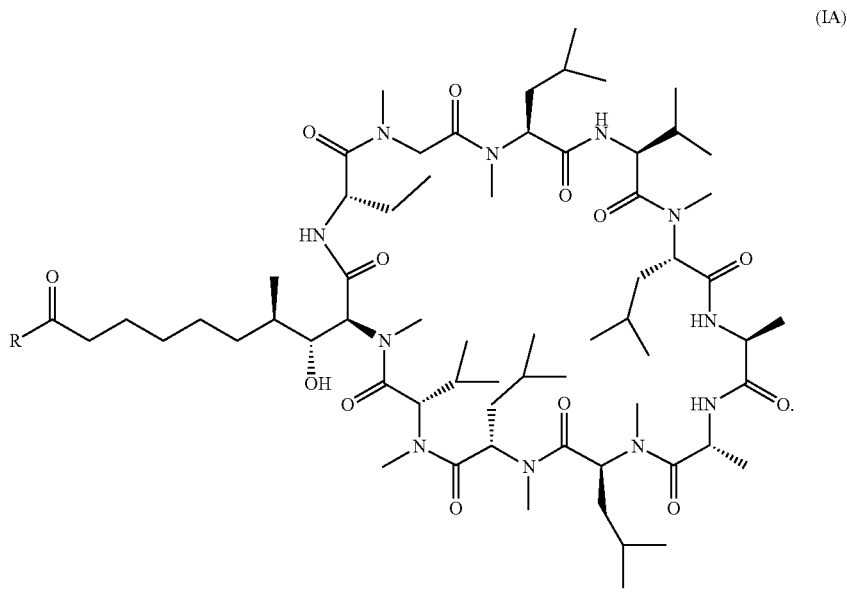

In some embodiments, the present disclosure relates to a pharmaceutical composition comprising the compound and a pharmaceutically acceptable carrier.

In one aspect, the present disclosure relates to a method for treating a disease associated with neutrophil-mediated inflammation in a target tissue of a mammalian subject in need thereof, comprising administering to the subject a therapeutically effective amount of a compound of Formula I:

(I)

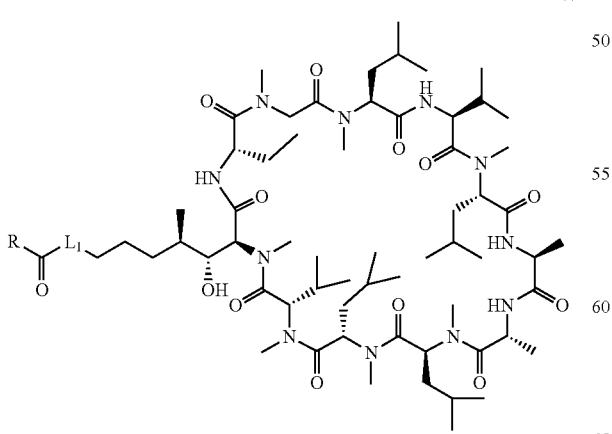

or a pharmaceutically acceptable salt thereof; wherein $L_1$ is a $C_0$ to $C_4$ alkyl group optionally substituted with one or more F; R is selected from the group consisting of —OH and a PEG, wherein the PEG optionally comprises a linker group, $L_2$ as defined herein. In some embodiments the PEG group has from 40 to 50 ethylene oxide units and $L_2$ is a substituted or unsubstituted heteroalkylene group such as an unsubstituted aminoalkylene group. In some embodiments, R is selected from —OH or —NH(CH$_2$)$_{2-6}$(CH$_2$CH$_2$O)$_{42-46}$—O(CH$_2$)$_{0-5}$CH$_3$. In some embodiments, R is selected from the group consisting of CH$_3$O—(CH$_2$CH$_2$O)$_{44}$—CH$_2$CH$_2$CH$_2$NH— (BT051), CH$_3$O—(CH$_2$CH$_2$O)$_{44}$—CH$_2$CH$_2$NH— (BT090), and HO— (BT070).

In some embodiments, $L_1$ may be ethylene and the compound of Formula I has the Formula IA:

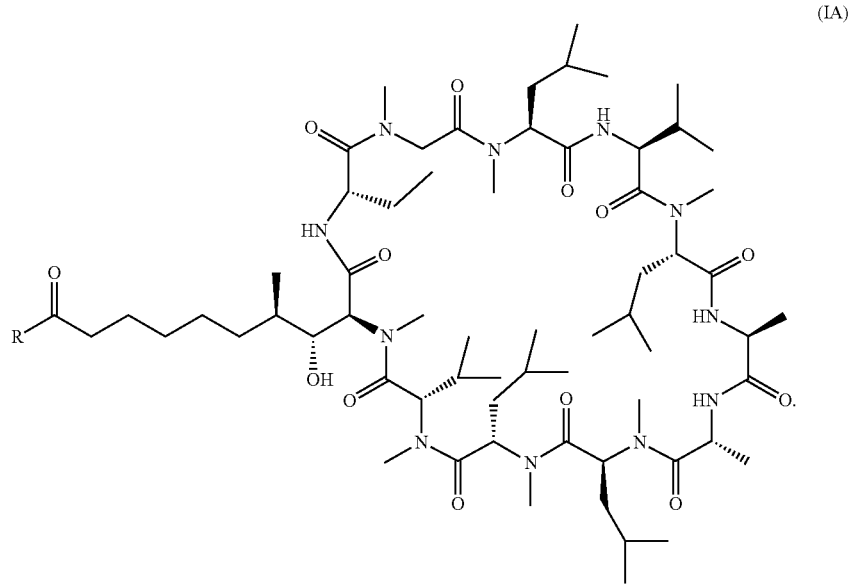

(IA)

In some embodiments, the disease is selected from the group consisting of intestinal disease, colitis, inflammatory lung disease, inflammatory skin disease, ocular disease, urogenital disease, and sexually transmitted diseases.

In some embodiments, the intestinal disease is selected from the group consisting of proctitis, orchitis, Crohn's disease, and celiac disease.

In some embodiments, the colitis is selected from the group consisting of ulcerative colitis, also known as colitis ulcerosa, infectious/non-infectious enterocolitis, and inflammatory bowel disease (IBD).

In some embodiments, the inflammatory lung disease is selected from the group consisting of pneumococcal infection, asthma, chronic obstructive pulmonary disease (COPD), and pulmonary fibrosis.

In some embodiments, the inflammatory skin disease is selected from the group consisting of dermatitis (eczema), rosacea, seborrheic dermatitis, and psoriasis.

In some embodiments, the ocular disease is selected from the group consisting of uveitis, retinitis, keratitis, and macular degeneration.

In some embodiments, the urogenital disease comprises a urinary tract infection.

In some embodiments, the sexually transmitted disease is selected from the group consisting of pelvic inflammatory disease, gonorrhea infection, chlamydia infection, herpes, and urethritis.

In some embodiments, the administering step is selected from the group consisting of topical administration and administration at a luminal surface of the target tissue.

In some embodiments, the inflammation is non-infectious inflammation. In some embodiments, the inflammation is infectious inflammation.

In some embodiments, the method further comprises administering to the subject a therapeutically effective amount of one or more second compound that inhibits one or more of multidrug resistance protein 2 (MRP2) and HXA$_3$ synthase, wherein the therapeutic amount of the second compound reduces migration of neutrophils into the target tissue.

In some embodiments, the method further comprises administering to the subject a therapeutically effective amount of one or more compounds that increases multidrug resistance protein 1 (MRP1), wherein the therapeutic amount of the third compound reduces migration of neutrophils into the target tissue.

In some embodiments, the method further comprises administering one or more compounds that inhibits one or more of multidrug resistance protein 2 (MRP2) and hepoxilin A3 (HXA$_3$) synthase, wherein the therapeutic amount of the second compound reduces migration of neutrophils into the target tissue.

In some embodiments, the method further comprises administering to the subject a therapeutically effective amount of one or more compounds that increases one or more N-acylethanolamines (NAEs), wherein the therapeutic amount of the third compound reduces migration of neutrophils into the target tissue.

In some embodiments, the inflammation is associated with Crohn's disease and the treatment or prevention further comprises administering one or more mesalamine products, corticosteroid formulations, ileal-release budesonide, glucocorticosteroids/EEN immunomodulatives, including azathioprine, 6-mercaptopurine, and methotrexate, anti-tumor necrosis factor (TNF) drugs, including infliximab, adalimumab, and certolizumab, pegol, anti-alpha-4 beta-7 integrin antibody vedolizumab, ABT-494, and filgotinib.

In some embodiments, the inflammation is associated with ulcerative colitis and the treatment or prevention further comprises administering one or more of 5-aminosalycylates, mesalamine, corticosteroids, multimatrix budesonide, azathioprine, 6-mercaptopurine, anti-TNF drugs, including infliximab, adalimumab, and golimumab, vedolizumab, tofacitinib, ABT-494, and filgotinib.

In some embodiments, the method further comprises administering one or more antibiotic and/or anti-inflammatory agents selected from the group consisting of: Dalbavancin, Oritavancin, Cubicin, Tedizolid, Ceftobiprole, Ceftobiprole, Ceftolozane-tazobactam, mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometholone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the method further comprises administering one or more antibodies selected from the group consisting of: antibodies targeting *Clostridium difficile* toxins, antibodies targeting tumor necrosis factor (TNF), antibodies targeting interleukins, and antibodies targeting metalloproteinase-9.

In some embodiments, the compound of Formula I reduces migration of neutrophils into the target tissue as compared to untreated control tissue.

BRIEF DESCRIPTION OF THE DRAWINGS

FIG. 2A is a chart showing the stability of BT090 in simulated intestinal fluid (SIF). FIG. 2B is a chart showing the stability of BT090 in simulated gastric fluid (SGF). FIG. 2C is a chart showing the stability of BT090 in feces.

FIGS. 3A and 3B are charts showing the inhibition of formyl peptide receptor 1 (FPR1) by BT051 (FIG. 3A) and BT051 and BT070 (FIG. 3B) as measured by the inhibition of fMLP-mediated neutrophil transmigration/activation.

DETAILED DESCRIPTION

I. Definitions

Figure 1:
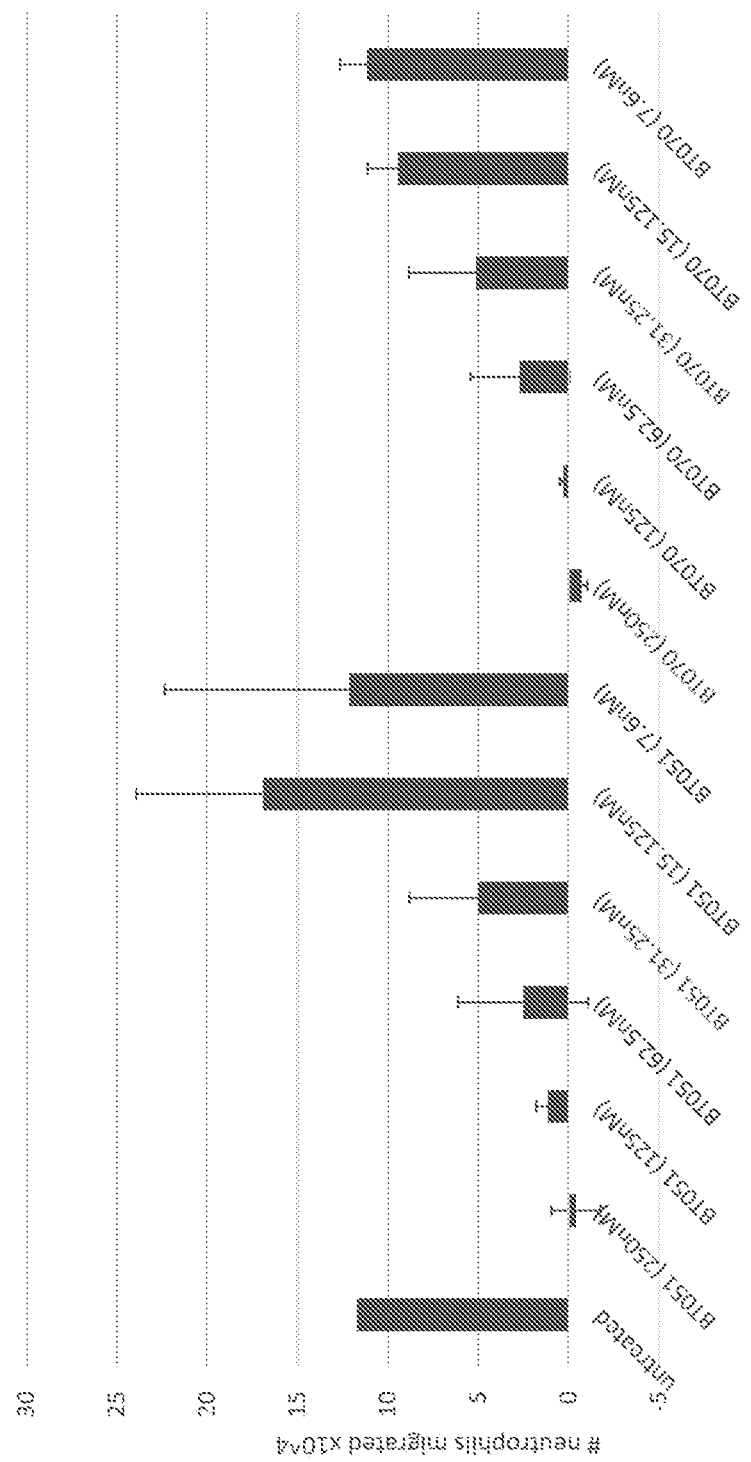
FIG. 1 is a chart showing the dose-response of BT051 and BT070 on the inhibition of neutrophil migration.

The following terms are used herein, the definitions of which are provided for guidance.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. It will be understood by those of skill in the art that substituted groups of the present technology are chemically stable groups that allow isolation of the compounds in which they appear. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; sulfonamides; amines; N-oxides; azides; amides; ureas; amidines; guanidines; nitro groups; nitriles (i.e., CN); and the like.

Alkyl groups include straight chain and branched chain alkyl groups having (unless indicated otherwise) from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. In some embodiments the alkyl group is substituted with 1, 2, or 3 substituents.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Heteroalkyl groups and heteroalkenyl groups are, respectively, alkyl groups (as defined herein) and alkenyl groups (as defined herein) that include from 1 to 6 heteroatoms selected from N, O and S. It will be understood that each heteroatom present is bonded to at least one carbon atom within the heteroalkyl or heteroalkenyl group. In some embodiments the heteroaklyl or heteteroalkenyl groups include 1, 2, or 3 heteroatoms. Heteroalkyl and heteroalkenyl groups may be substituted or unsubstituted. Examples of heteroalkyl groups include but are not limited to CH$_3$CH$_2$OCH$_2$, CH$_3$NHCH$_2$, CH$_3$CH$_2$N(CH$_3$)CH$_2$, CH$_3$CH$_2$SCH$_2$, CH$_3$CH$_2$OCH$_2$CH$_2$OCH$_2$CH$_2$. Examples of heteroalkenyl groups include but are not limited to CH$_2$═CHOCH$_2$, CH$_2$═CHN(CH$_3$)CH$_2$, and CH$_2$═CHSCH$_2$. Representative substituted heteroalkyl or heteroalkeneyl groups may be substituted one or more times with substituents such as those listed above (e.g., 1, 2 or 3 times), and include without limitation haloheteroalkyl (e.g., trifluoromethyloxyethyl), carboxyalkylaminoalkyl, methyl acrylate and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent cycloalkyl groups are cycloalkylene groups, divalent heteroalkyl groups are heteroalkylene groups, divalent alkenyl groups are alkenylene groups, and so forth. Substituted groups having a single point of attachment to the compound of the present technology are not referred to with the "ene" designation. Thus, e.g., chloroethyl is not referred to herein as chloroethylene.

The term "administering" a molecule to a subject means delivering the molecule to the subject. "Administering" includes prophylactic administration of the composition (i.e., before the disease and/or one or more symptoms of the disease are detectable) and/or therapeutic administration of the composition (i.e., after the disease and/or one or more symptoms of the disease are detectable). The methods of the present technology include administering one or more compounds. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

The terms "alter" and "modify" when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), refer to an increase and/or decrease.

"Cannabinoid receptor type 2" ("CB2") is a G protein-coupled receptor from the cannabinoid receptor family that in humans is encoded by the CNR2 gene. The principal endogenous ligand for the CB2 receptor is 2-arachidonoylglycerol (2-AG).

Use of the terms "comprising", "including" or similar terms to describe or define an embodiment of a compound, composition or method having one or more elements shall be understood to also disclose embodiments "consisting" or "consisting essentially" of the elements and vice versa. In other words, disclosure of embodiments open to elements beyond those listed ("comprising"), also are to be understood to disclose embodiments which are closed to additional elements ("consisting") or which may only include additional elements that do not materially affect the characteristics of the embodiment ("consisting essentially"). Likewise, embodiments consisting or consisting essentially of the listed elements shall be understood to disclose embodiments comprising those elements.

The term "conjugating," and grammatical equivalents, when made in reference to conjugating a molecule of interest and a polymer means covalently linking the molecule of interest to the polymer. Linkage may be direct. Alternatively, linkage may be indirect via a linking group or moiety. Methods for conjugation to polymers are known in the art, including methods for conjugation to a polypeptide to produce a fusion protein (Pasut, *Polymers* 6:160-178 (2014); Medscape, *Nanomedicine* 5(6):915-935 (2010)). In some embodiments, the conjugate comprises cyclosporine A conjugated to a PEG polymer. Precursors to such cyclosporine A conjugates, include cyclosporine A modified, e.g., with a linking group, but without the PEG polymer. The linking group links the polymer to the cyclosporine A.

As used herein, the terms "effective amount" or "therapeutically effective amount," or "pharmaceutically effective amount" refer to a quantity sufficient to achieve a desired therapeutic and/or prophylactic effect, e.g., an amount which results in the full or partial amelioration of inflammation (e.g., inflammation associated with neutrophil migration into a target tissue) or disease or disorders or symptoms associated with inflammation in a subject in need thereof. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In some embodiments, multiple doses are administered. Additionally or alternatively, in some embodiments, multiple therapeutic compositions or compounds are administered. In the methods described herein, the therapeutic compounds may be administered to a subject having one or more signs or symptoms of a disease or disorder associated with inflammation (e.g., inflammation associated with increased neutrophil migration into a tissue).

"Endocannabinoids" ("ECs") are compounds that bind to the cannabinoid receptors, CB1 and CB2, as well as more recently described atypical receptors GPR55 and GPR119. The two main classes of eicosanoid-type ECs are "N-acyl-lethanolamines" ("NAEs") and monoacylglycerols (MAGs), which are metabolized by fatty acid amide hydrolase (FAAH) and monoacyl glycerol lipase (MAGL), respectively. "N-acylethanolamine" is an endocannabinod and is a type of fatty acid amide formed when one of several types of acyl group is linked to the nitrogen atom of ethanolamine. N-acylethanolamines are metabolized by fatty acid amide hydrolase (FAAH). Exemplary N-acylethanolamine endocannabinoids include ethanolamine, anandamide (AEA) (N-arachidonoylethanolamine), which is the amide of arachidonic acid (20:4 ω-6) oleoyl ethanolamide (OEA), and alpha-linolenoyl ethanolamide (α-LEA).

"Fatty acid amide hydrolase," "FAAH," and "EC 3.5.1.99" interchangeably refer to a member of the serine hydrolase family of enzymes. It was first shown to break down anandamide. In humans, it is encoded by the gene FAAH.

"Hepoxilin A3 synthase," "HXA$_3$ synthase," "ALOX12," "12-lipoxygenase," "arachidonate 12-lipoxygenase," "12S-Lipoxygenase," "12-LOX," and "12S-LOX" interchangeably refer to a lipoxygenase-type enzyme (i.e., an enzyme that catalyzes the dioxygenation of polyunsaturated fatty acids in lipids containing a cis,cis-1,4-pentadiene structure) that in humans is encoded by the ALOX12 gene, which is located along with other lipoyxgenases on chromosome 17p13.3.

The term "increase" when in reference to a compound e.g., N-acylethanolamine, means increase the level and/or activity of N-acylethanolamine. The terms "increase," "elevate," "raise," and grammatical equivalents (including "higher," "greater," etc.) when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

The term "inhibit" when used in reference to a compound, e.g., multidrug resistance protein 2 (MRP2), hepoxilin A3 (HXA$_3$) synthase, etc., means inhibit the activity and/or level of HXA$_3$. The terms "inhibit," "reduce," "diminish," "suppress," "decrease," and grammatical equivalents (including "lower," "smaller," etc.) when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell, and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

"Multidrug resistance-associated protein 2," "multidrug resistance protein 2" ("MRP2"), "canalicular multispecific organic anion transporter 1" ("cMOAT"), "ATP-binding cassette sub-family C member 2" ("ABCC2") are interchangeably used to refer to protein that in humans is encoded by the ABCC2 gene.

"Multidrug resistance protein 1," "MRP1" and "ABCC1" are interchangeably used to refer to a uni-directional efflux transporter protein with a wide substrate specificity including important therapeutics. Some of the main roles of this transporter are: (i) efflux of xenobiotic and endogenous metabolites; (ii) transport of inflammatory mediators (e.g., LTC4); and (iii) defense against oxidative stress. The 190-kDa MRP1 has a core structure consisting of two transmembrane domains (TMD), each followed by a nucleotide binding domain (NBD). In common with MRP2, 3, 6, and 7, MRP1 contains a third TMD (TMDO) with five predicted trans membrane segments and an extra cytosolic $NH_2$ terminus connected to the core structure by a linker region (L0) (Rosenberg et al., *J. Biol. Chem.* 276(19):13076-16082 (2001)). The TMDO appears to be important for MRP1 trafficking to the plasma membrane (Bakos et al., *J. Cell Sci.* 113(Pt 24):4451-4461 (2000)), and the precise roles, mechanisms, and dependencies of TMDO and L0 are the subject of significant research (Westlake et al. *Mol. Biol. Cell* 16(5): 2483-2492 (2005)). MRP1 has broad substrate specificity, transporting hydrophobic and anionic molecules, glucuronide and glutathione conjugates, as well as endogenous glutathione. Although many MRP1 substrates are conjugated to glutathione, co-transport of free glutathione is often observed, and appears to stimulate transport of e.g., vincristine and daunorubicin (Hooijberga et al., *FEBS Letters* 469:47-51(2000)). Glutathione itself is a low affinity substrate of MRP1 (Km=1-5 mM). Multiple allosterically cooperative, non-overlapping substrate-binding sites are postulated, which may explain why various substrates both cross-inhibit and cross-stimulate (Bakos et al., *Pflugers Arch—Eur J Physiol* 453:621-641(2007)). The inflammatory cytokine LTC4 and its main metabolite LTD4 are some of the highest affinity MRP1 substrates, suggesting a key role for MRP1 in cytokine release from LTC4 producing cells. In fact, intracellular LTC4 accumulation was observed in mrp1 (−/−) mice (Robbiani et al., *Cell* 103:757-768 (2000)). Additionally, although viable, healthy, and fertile with normal phenotype, knockout mrp1 (−/−) mice were hypersensitive to cytotoxic drugs (Wijnholds et al., *Nat. Med.* 3:1275-1279 (1997)). MRP1 is exemplified by the human protein sequence NCBI Reference Sequence: NP_004987.2 encoded by the DNA sequence NCBI Reference Sequence: NG_028268.1. There are at least 15 naturally occurring mutations identified in MRP1, and many of them have been found to affect its in vitro transport activity. Polymorphisms and mutagenesis studies have been reviewed in He et al., *Curr. Med. Chem.* 18:439-481 (2011). Although many MRP1 SNPs are known, their incidence in populations is reported to be relatively low. In mainland Chinese populations the MRP1 polymorphism allelic frequencies of Cys43Ser (128G>C), Thr73Ile (218C>T), Arg723Gln (2168G>A) and Arg1058Gln (3173G>A) were 0.5%, 1.4%, 5.8% and 0.5%, respectively (Ji-Ye Yin et al., *Pharmacogenet. Genomics* 19(3):206-216 (2009)).

"P-glycoprotein" ("P-gp") is an efflux membrane transporter, and is responsible for limiting cellular uptake and the distribution of xenobiotics and toxic substances.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

"Polymer" is a substance that has a molecular structure consisting chiefly or entirely of a large number of similar units bonded together. Polymers may occur naturally (e.g., cellulose, polypeptides, nucleotides sequences, etc.) or are artificial (e.g., plastics, resins, etc.). Polymers may be used as carriers of drugs to which they are conjugated, and may enhance the solubility of the conjugated drug, improve its pharmacokinetic profile, protect the drug against degradation, release the drug under certain conditions, such as change in pH or in the presence of enzymes, such as esterases, lipases or proteases. In addition, a targeting moiety or a solubilizer may also be introduced into the conjugate to boost its therapeutic index (Medscape, *Nanomedicine* 5(6):915-935(2010)). Polymers may also be utilized to restrict the distribution of the drug conjugated to it by, for example, preventing the conjugated drug from crossing into specific body compartments (e.g., from the gastrointestinal lumen to the underlying tissue). Polymers may be natural polymers and/or synthetic linear polymers, and include polyethylene glycol (PEG), dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly(hydroxyalkylmethaacrylamide), polyglycerol, 25 polyamidoamine (PAMAM), polyethylenimine (PEI), and polypeptides.

"SipA" and "Salmonella T3SS effector protein" are used interchangeably to refer to a protein produced by Salmonella, as exemplified by the amino acid sequence of Salmonella enterica subsp. enterica serovar Typhimurium str. SL1344 (GenBank: AAA86618.1) encoded by the DNA sequence (Locus taq) SL1344_2861 of the Salmonella enterica subsp. enterica serovar Typhimurium str. SL1344, complete genome sequence (NCBI Reference Sequence: NC_016810.1). The SipA sequence is provided by WO 2015/089268.

"Target tissue" that may suffer from inflammation includes, without limitation, epithelial tissue, mucosal tissue, etc. Exemplary epithelial tissue and/or mucosal tissue include gastrointestinal, lung (e.g., bronchial tissue), liver, stomach, colon, brain, gallbladder, renal, female genital tract, ocular, urinary tract, etc., resulting in "inflammatory diseases" such as intestinal disease (exemplified by proctitis, orchitis, Crohn's disease, colitis (such as ulcerative colitis, also known as colitis ulcerosa), infectious/non-infectious enterocolitis, inflammatory bowel disease (IBD), etc.), inflammatory lung conditions (such as pneumococcal infection, asthma, chronic obstructive pulmonary disease (COPD), and pulmonary fibrosis), inflammatory skin diseases (such as dermatitis (eczema), rosacea, seborrheic dermatitis, and psoriasis), ocular disease (exemplified by uveitis, retinitis, keratitis, macular degeneration, etc.), urogenital disease (such as urinary tract infection), sexually transmitted diseases (such as pelvic inflammatory disease that includes inflammatory disease exemplified by gonorrhea infection and/or chlamydia infection, and by ulceration disease exemplified by herpes), urethritis, etc. As used herein, "target tissue" also encompasses an anatomic space, e.g., the intestinal lumen.

"Treating," "treat," "treated," or "treatment" as used herein covers the treatment of a disease or disorder described herein (e.g., inflammation), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. Symptoms may be assessed by methods known in the art, for example, biopsy and histology, and blood tests to determine relevant enzyme levels, metabolites or circulating antigen or antibody (or other biomarkers), quality of life questionnaires, patient-reported symptom scores, and imaging tests.

As used herein, "prevention" or "preventing" of a disorder or condition refers to a compound that, in a statistical sample, reduces the occurrence of the disorder or condition in the treated sample relative to a control sample, or delays the onset of one or more symptoms of the disorder or condition relative to the control sample.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, ave, etc. In some embodiments, the mammal is murine. In some embodiments, the mammal is human.

A subject "in need" of treatment according to the methods and/or compositions of the present technology includes a subject that is "suffering" from inflammation (i.e., a subject that is experiencing and/or exhibiting one or more clinical and/or subclinical symptoms of inflammation), and a subject "at risk" of inflammation. A subject "in need" of treatment includes animal models of inflammation. Subject "at risk" of inflammation refers to a subject that is not currently exhibiting inflammation symptoms and is predisposed to expressing one or more symptoms of the disease. This predisposition may be based on family history, genetic factors, environmental factors such as exposure to detrimental compounds present in the environment, etc. It is not intended that the present technology be limited to any particular signs or symptoms. Thus, it is intended that the present technology encompass subjects that are experiencing any range of disease, from sub-clinical symptoms to full-blown inflammatory disease, wherein the subject exhibits at least one of the indicia (e.g., signs and symptoms) associated with the inflammatory disease.

"Substantially the same," "without substantially altering," "substantially unaltered," and grammatical equivalents, when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) means that the quantity of molecule, cell, and/or phenomenon in the first sample (or in the first subject) is neither increased nor decreased by a statistically significant amount relative to the second sample (or in a second subject). Thus, in one embodiment, the quantity of molecule, cell, and/or phenomenon in the first sample (or in the first subject) is from 90% to 100% (including, for example, from 91% to 100%, from 92% to 100%, from 93% to 100%, from 94% to 100%, from 95% to 100%, from 96% to 100%, from 97% to 100%, from 98% to 100%, and/or from 99% to 100%) of the quantity in the second sample (or in the second subject).

As used herein, "weight percent" of a component, unless specifically stated to the contrary, is based on the total weight of the formulation or composition in which the component is included.

II. General

In one aspect, the present technology the present technology provides methods, compounds, and compositions for inhibiting formyl peptide receptor 1 (FPR1) and for treating disease associated with FPR1 activation. In some embodiments, disease associated with FPR1 activation comprises celiac disease.

In one aspect, the present technology provides methods, compounds, and compositions for treating neutrophil-mediated inflammation and disease associated with neutrophil-mediated inflammation. In particular, the present technology provides a method for treating neutrophil-mediated inflammation in a target tissue of a mammalian subject in need thereof, comprising administering to the subject a therapeutically effective amount of one or more first compound that increases the level and/or activity of multidrug resistance protein 1 (MRP1), wherein the therapeutic amount of the first compound reduces migration of neutrophils into the target tissue, and/or administering a therapeutically effective amount of one or more second compound that inhibits one or more of multidrug resistance protein 2 (MRP2), and hepoxilin A3 (HXA$_3$) synthase, wherein the therapeutic amount of the second compound reduces migration of neutrophils into the target tissue, and/or administering a therapeutically effective amount of one or more third compound that increases one or more N-acylethanolamines (NAEs), wherein the therapeutic amount of the third compound reduces migration of neutrophils into the target tissue.

In one embodiment, the present disclosure provides methods for treating neutrophil-mediated inflammation by targeting the pro-inflammatory MRP2/HXA$_3$ pathway, comprising administering to the subject a therapeutically effective amount of one or more compound that inhibits the activity and/or level of one or more of multidrug resistance protein 2 (MRP2) and hepoxilin A3 (HXA$_3$) synthase, wherein the therapeutic amount of the compound reduces migration of neutrophils into the target tissue.

In another embodiment, the present disclosure also provides methods for treating neutrophil-mediated inflammation by targeting the anti-inflammatory P-gp/endocannabinoid pathway, comprising administering to the subject a therapeutically effective amount of one or more compound that increases the level and/or activity of one or more N-acylethanolamines (NAEs), wherein the therapeutic amount of the compound reduces migration of neutrophils into the target tissue.

In a further embodiment, the present disclosure further provides methods for treating neutrophil-mediated inflammation, comprising administering to the subject a therapeutically effective amount of one or more second compound that increases the level and/or activity of multidrug resistance protein 1 (MRP1), wherein the therapeutic amount of the compound reduces migration of neutrophils into the target tissue In yet another embodiment, the present disclosure provides methods for treating neutrophil-mediated inflammation by targeting both the anti-inflammatory P-gp/endocannabinoid, and the pro-inflammatory MRP2/HXA$_3$ pathway, the method comprising administering to the subject a therapeutically effective amount of (A) one or more first compound that inhibits the activity and/or level of one or more of multidrug resistance protein 2 (MRP2) and hepoxilin A3 (HXA$_3$) synthase, and (B) one or more second compound that increases the level and/or activity of one or more N-acylethanolamines (NAEs), wherein the therapeutic amount of the first and second compounds reduces migration of neutrophils into the target tissue.

III. Compounds of the Present Technology

The present technology provides compositions for treating neutrophil-mediated inflammation and conditions associated therewith. In some embodiments, the present technology provides compositions comprising one or more of a first compound that increases the level and/or activity of multidrug resistance protein 1 (MRP1), a second compound that inhibits one or more of multidrug resistance protein 2 (MRP2) and hepoxilin A3 (HXA$_3$) synthase, and/or a third compound that increases one or more N-acylethanolamines (NAEs).

In some embodiments, the present technology discloses a cyclosporine A-polymer conjugate and precursor thereof defined by Formula I:

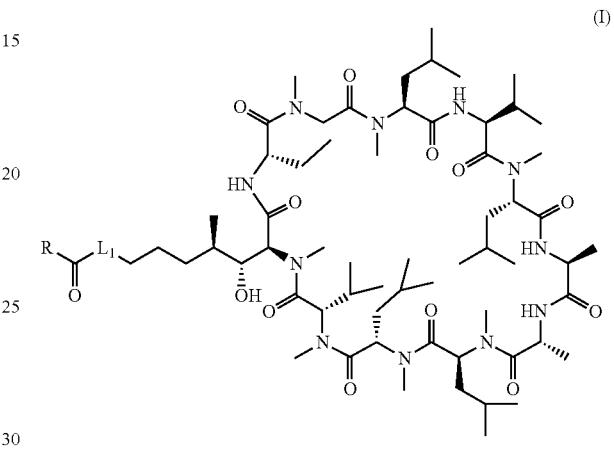

(I)

a stereoisomer thereof, or a pharmaceutically acceptable salt of any of the foregoing. In Formula I, L$_1$ may be a C$_0$ to C$_4$ alkyl group optionally substituted with one or more F. For example, in some embodiments, L$_1$ may be methylene, ethylene, propylene or butylene. In some embodiments, L$_1$ may be C$_0$. In some embodiments, L$_1$ may be C1-C4 fluoroalky. The fluoroalkyl may have 1, 2, 3, 4 or more F and/or may be perfluorinated. In Formula I, R may be —OH or a polymer, optionally including a linker group, L$_2$.

In some embodiments, the polymer of R is selected from the group consisting of dextran, polyethylene glycol (PEG), periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly (hydroxyalkylmethaacrylamide), polyglycerol, 25 polyamidoamine (PAMAM), polyethylenimine (PEI), and polypeptides. In some embodiments, the polymer is PEG. The PEG polymers may be functionalized with amine (NH$_2$) and/or aldehyde (CHO) that include linear mono-amines and monoaldehydes, linear bi-amines and bi-aldehydes, multi-arm-amines and multi-arm-aldehydes, branched mono-, bi- and multi-armed-amines and aldehydes and multi-arm-forked-amines and aldehydes. In some embodiments, the polymer is PEG having 40-50 ethylene oxide subunits, i.e., 40, 41, 42, 43, 44, 45, 46, 47, 48, 49 or 50 ethylene oxide subunits or a range between and including any two of the foregoing values. The polymers can be of any molecular weight as described herein.

In some embodiments, the polymer has an average molecular weight in the range of about 100 Da to about 800 kDa. (Unless otherwise indicated, "average molecular weight" means weight average molecular weight.) In some embodiments the polymer has an average molecular weight in the range of about 1 kDa to about 800 kDa. In some embodiments, the polymer has an average molecular weight less than 1 kDa. In some embodiments, the polymer has an average molecular weight less than 10 kDa. In some embodiments, the average molecular weight of the polymer is about 1 kDa, 2 kDa, 5 kDa, 10 kDa, 20 kDa, 30 kDa, 40 kDa, 50 kDa, 60 kDa, 70 kDa, 80 kDa, 90 kDa, 100 kDa, 125 kDa, 150 kDa, 175 kDa, 200 kDa, 225 kDa, 250 kDa, 275 kDa, 300 kDa, 325 kDa, 350 kDa, 375 kDa, 400 kDa, 425 kDa, 450 kDa, 475 kDa, 500 kDa, 550 kDa, 600 kDa, 650 kDa, 700 kDa, 750 kDa, 800 kDa, or any range between and including two of these values.

The polymers described herein can have any of a number of different geometries. For example, in some embodiments, the polymers are linear polymers, branched polymers, forked polymers, or a combination of any of these polymers.

As noted above, the R group in the compound of Formula I (or IA) optionally includes a linker, $L_2$. In some embodiments, the linker $L_2$ is a biodegradable linker. In some embodiments, the biodegradable linker comprises an oligopeptide having from 2 to 10 amino acid residues. The residues may be selected from the naturally occurring amino acids.

In some embodiments, the linker $L_2$ comprises a substituted or unsubstituted $C_1$-$C_x$ alkylene, cycloalkylene, cycloalkylalkylene, heteroalkylene, alkenylene, or heteroalkenylene group, wherein x may be any integer from 1 to 12, i.e., 1, 2, 3, 4, 5, 6, 7, 8, 9, 10, 11 or 12. For example, $L_2$ may comprise a $C_1$-$C_x$ fluoroalkyl group where one or more of the hydrogen atoms are fluorine atoms, such as 1, 2 or 3 or more fluorines. In some embodiments, $L_2$ may be a heteroalkylene containing one or two NH groups, including but not limited to ($C_1$-$C_{10}$ alkylene)-NH (e.g., $CH_2CH_2NH$, $CH_2CH_2CH_2NH$, $CH_2CH_2CH_2CH_2NH$, $CH_2CH(CH_3)CH(CH_3)CH_2NH$), (Cn alkylene)NH($C_p$ alkylene) where n, p are independently an integer from 1-10, but n+p does not exceed 10 (e.g., $CH_2CH_2CH_2NHCH_2CH_2$), NH—($C_1$-$C_{10}$ alkylene)NH (e.g., $NH(CH_2)_5NH$, $NH(CH_2)_6NH$, $NH(CH_2)_8NH$), or NH(Cn alkylene)NH($C_p$ alkylene) where n and p are integers as defined previously (e.g., $NHCH_2CH_2CH_2NH\ CH_2CH_2$, $NH(CH_2)_6NHCH_2$). In some embodiments, the $L_2$ may be a heteroalkylene that contains one or two oxygen atoms, including but not limited to ($C_1$-$C_{10}$ alkylene)-O (e.g., $CH_2CH_2O$, $CH_2CH_2CH_2O$, $CH_2CH_2CH_2CH_2O$, $CH_2CH(CH_3)CH(CH_3)CH_2O$), (Cn alkylene)O($C_p$ alkylene) where n, p are independently an integer from 1-10, but n+p does not exceed 10 (e.g., $CH_2CH_2CH_2OCH_2CH_2$), O—($C_1$-$C_{10}$ alkylene)O (e.g., $O(CH_2)_{50}$, $O(CH_2)_{60}$, $O(CH_2)_8O$), or O(Cn alkylene)O($C_p$ alkylene) where n and p are integers as defined previously (e.g., $OCH_2CH_2CH_2O\ CH_2CH_2$, $O(CH_2)_6OCH_2$). In some embodiments, $L_2$ may be a heteroalkylene containing an O and an NH group, including but not limited to NH—($C_1$-$C_{10}$ alkylene)O, (e.g., $NH(CH_2)_5O$, $NH(CH_2)_6O$, $NH(CH_2)_8O$), or NH(Cn alkylene)O($C_p$ alkylene) where n and p are integers as defined previously (e.g., $NHCH_2CH_2OCH_2CH_2$, $O(CH_2)_6NHCH_2$).

In some embodiments of the compound of Formula I (including Formula IA) R is —OH or a PEG group having from 40 to 50 ethylene oxide units and includes a linker, $L_2$, that is a substituted or unsubstituted heteroalkylene group, e.g., an unsubstituted aminoalkylene group. In some embodiments, R is selected from —OH or —NH$(CH_2)_{2-6}$—$(CH_2CH_2O)_{42-46}$—$O(CH_2)_{0-5}CH_3$. In some embodiments, R is selected from the group consisting of $CH_3O$—$(CH_2CH_2O)_{44}$—$CH_2CH_2CH_2NH$— (BT051), $CH_3O$—$(CH_2CH_2O)_{44}$—$CH_2CH_2NH$— (BT090), and HO— (BT070). In any such embodiments m may be 2 and have the structure of Formula IA.

The cyclosporine A-polymer conjugates and precursors may be prepared using standard techniques known in the art. In some embodiments, a difunctional linker containing at least two functional groups containing heteroatoms selected from N, O, and S in which one of the functional groups is protected may be conjugated using standard ester, thioester and amide bond forming technology. For example, a diamino-alkylene linker in which one of the amino groups is protected by a urethane protecting group (e.g., Boc. Cbz, etc.) may be coupled to cyclosporine A in the presence of a coupling agent (e.g., DCC, EDC/HOBt, etc.). Alternatively, an active ester, mixed anhydride or acid halide derivative of cyclosporine A may be prepared and reacted with the mono-protected diamine. (See, for example, Bodansky, M. & Bodanszky, A., *The Practice of Peptide Synthesis*, Springer-Verlag, New York, 1984.) The protecting group may be removed and the free amine reacted with an aldehyde derivative of the polymer under reducing conditions to provide the conjugate. Similarly, a linker with a protected aldehyde (e.g., 1,1-dimethoxy) and an amine may be coupled to the cyclosporine A, deprotected to form the aldehyde and subjected to reductive amination with an amino-bearing polymer to form the conjugate. Variations of these schemes using α,ω-carboxy amines, α,ω-aminoalcohols, α,ω-carboxyalcohols, α,ω-aminothiols, and the like to link cyclosporine A and the polymer will be readily understood by those of skill in the art.

In some embodiments, cyclosporine A compounds of the present technology are used in combination with one or more compounds that increase (multidrug resistance protein 1) MRP1 for the treatment of inflammatory disease.

In some embodiments, cyclosporine A compounds of the present technology are used in combination with one or more multidrug resistance protein 2 (MRP2) inhibitors for the treatment of inflammatory disease. In some embodiments, the MRP2 inhibitor is selected from the group consisting of MRP2 RNAi; 3-([3-(2-[7-chloro-2-quinolinyl] ethenyl)phenyl-(3-dimethylamino-3-oxopropyl)-thio-methyl]thio)propanoic acid (also known as "MK571" and CysLT1 (LTD4) leukotriene receptor inverse agonist) (Tocris, Minneapolis, USA) (Genuuso et al. (2004) PNAS 101: 2470-2475); Probenecid (also known as "PROBALAN™"), exemplified by probenecid inhibition of MRP2; FUROSEMIDE®; RITONAVIR®; SAQUINAVIR®; LAMIVUDINE®; ABACAVIR®; EMTRICITABINE®; EFAVIRENZ®; DELAVIRDINE®; NEVIRAPINE®; CIDOFOVIR®; ADEFOVIR®; and TENOFOVIR®. In some embodiments, the compound is conjugated to a polymer.

In some embodiments, the compound that inhibits the MRP2 comprises one or more of a compound that inhibits Hepoxilin A3 synthase, such as Hepoxilin A3 synthase RNAi. In some embodiments, the compound is conjugated to a polymer.

In some embodiments, the compound that inhibits the MRP2 comprises one or more compounds that inhibit fatty acid amide hydrolase (FAAH), such as FAAH RNAi; FAAH Inhibitor I (PubChem CID: 295380) 4-phenylmethoxyphenyl)N-butylcarbamate); URB597(PubChem CID: 1383884) 3'-Carbamoyl-[1,1'-biphenyl]-3-yl cyclohexylcarbamate; FAAH inhibitor 1 (PubChem CID: 1190414)N-(4-(6-methylbenzo[d]thiazol-2-yl)phenyl)-1-(thiophen-2-ylsulfonyl) piperidine-4-carboxamide; FAAH Inhibitor, 2l (PubChem CID:71699786); FAAH Inhibitor, 2i (PubChem CID: 71699785)N-Cyclohexylcarbamic acid 4-(dimethylamino)-3-phenylphenyl ester; FAAH Inhibitor, 2 h (PubChem CID: 71699784)N-Cyclohexylcarbamic acid 4-(hydroxymethyl)-

3-phenylphenyl ester; FAAH Inhibitor, 2j (PubChem CID: 58801136); FAAH Inhibitor, 2e (PubChem CID: 58801135); FAAH Inhibitor, 2a (PubChem CID: 58801134); FAAH Inhibitor, 2b (PubChem CID: 58801129); FAAH Inhibitor, 2f (PubChem CID: 58801126) Carbamic acid, cyclohexyl-, 6-methyl[1,1'-biphenyl]-3-yl ester; FAAH Inhibitor, 2k (PubChem CID: 58801125); FAAH Inhibitor, 2c (PubChem CID: 57582480); FAAH Inhibitor, 2g (PubChem CID: 44626363); FAAH Inhibitor, 2d (PubChem CID: 44626362); AM374, palmitylsulfonyl fluoride; ARN2508, derivative of flurbiprofen; BIA 10-2474; BMS-469908; CAY-10402; JNJ-245; JNJ-1661010; JNJ-28833155; JNJ-40413269; JNJ-42119779; JNJ-42165279; LY-2183240; Cannabidiol; MK-3168; MK-4409; MM-433593; OL-92; OL-135; PF-622; PF-750; PF-3845; PF-04457845; PF-04862853; RN-450; SA-47; SA-73; SSR-411298; ST-4068; TK-25; URB524; URB597 (KDS-4103, Kadmus Pharmaceuticals); URB694; URB937; VER-156084; V-158866; and Multiple FAAH inhibitors from ChemCruz® Biochemicals, Dallas, Tex.). In some embodiments, the compound is conjugated to a polymer.

In some embodiments, the compound that inhibits the MRP2 comprises one or more compounds that inhibit P-glycoprotein (P-gp), such as P-gp RNAi; SipA; and small molecules (e.g., zosuquidar trihydrochloride (LY335979); VALSPODAR® (PSC833) (Inhibitor of P-gp-mediated MDR); CP 100356 hydrochloride (Sigma-Aldrich); and Elacridar hydrochloride (R&D Systems). See also, WO 2004071498 A1; WO 2014106021 A1; WO 2005033101 A1; WO 2004009584 A1; WO 2002030915 A2; US 20100029755 A1; and US 20060073196 A1). In some embodiments, the compound is conjugated to a polymer.

In some embodiments, cyclosporine A compounds of the present technology (including but not limited to compounds of Formulas I and IA) are used in combination with one or more compounds that increase N-acylethanolamines (NAEs) for the treatment of inflammatory disease. In some embodiments, the compound that increases NAEs is a cannabinoid receptor type 2 (CB2) "agonist" (i.e., a compound that specifically binds to, and activates, CB2). Illustrative CB2 agonists include GW-405,833; AM-1241; HU-308; JWH-015; JWH-133; L-759,633; L-759,656; beta-caryophyllene; arachidonylcyclopropylamide; and arachidonyl-2'-chloroethylamide. In some embodiments, the compound is conjugated to a polymer.

IV. Use of the Compositions of the Present Technology

The present technology provides methods for treating, preventing, or ameliorating neutrophil-mediated inflammation in a target tissue of a mammalian subject in need thereof, comprising administering to the subject a therapeutically effective amount of one or more first compound that inhibits one or more of multidrug resistance protein 2 (MRP2) and hepoxilin A3 (HXA$_3$) synthase, wherein the therapeutically effective amount of the first compound reduces migration of neutrophils into the target tissue. In some embodiments, the first compound is a cyclosporine A conjugate or precursor thereof such as, e.g., compounds of Formulas I or IA. In some embodiments, the method further comprises administering to the subject a therapeutically effective amount of one or more second compound that increases one or more N-acylethanolamines (NAEs), wherein the therapeutic amount of the second compound reduces migration of neutrophils into the target tissue. In a further embodiment, the method further comprises administering to the subject a therapeutically effective amount of one or more second and/or third compound that increases the level and/or activity of multidrug resistance protein 1 (MRP1), wherein the therapeutic amount of one or more second and/or third compound reduces migration of neutrophils into the target tissue. In another embodiment, the compounds of the present technology are administered singly or in any combination to a topical surface of the target tissue and/or at a luminal surface of the target tissue. In a further embodiment, the first compound that reduces migration of neutrophils into the target tissue is conjugated to a polymer. In another embodiment, the inflammation is non-infectious and/or infectious inflammation.

The present technology also provides methods for treating, ameliorating, or preventing neutrophil-mediated inflammation in a target tissue of a mammalian subject in need thereof, comprising administering to the subject a therapeutically effective amount of one or more first compound that increases one or more N-acylethanolamines (NAEs), wherein the therapeutic amount of the first compound reduces migration of neutrophils into the target tissue. In one embodiment, the method further comprises administering to the subject a therapeutically effective amount of one or more second compound that inhibits one or more of multidrug resistance protein 2 (MRP2) and HXA$_3$ synthase, wherein the therapeutic amount of the second compound reduces migration of neutrophils into the target tissue. In some embodiments, the second compound is a cyclosporine A conjugate or precursor thereof such as, e.g., compounds of Formulas I or IA. In another embodiment, the method further comprises administering to the subject a therapeutically effective amount of one or more second and/or third compound that increases the level and/or activity of multidrug resistance protein 1 (MRP1), wherein the therapeutic amount of the one or more second and/or third reduces migration of neutrophils into the target tissue. In a further embodiment, the one or more first compound that increases the one or more NAEs is a cannabinoid receptor type 2 (CB2) agonist. In another embodiment, the first compound that reduces migration of neutrophils into the target tissue is conjugated to a polymer.

In one aspect, the methods, compounds, and compositions of the present technology relate to cyclosporine A-polymer conjugates and precursors defined by Formula I as well as stereoisomers thereof, and pharmaceutically acceptable salts of any of the foregoing:

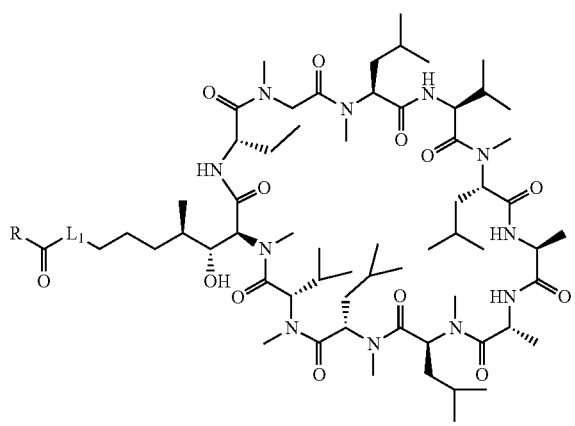

wherein L$_1$ and R may be as defined herein, as well as the use of one or more of these compounds (including but not limited to Formula IA, BT-051, BT-090, BT 122, BT 123, BT 125, and BT126) to treat, ameliorate, or prevent neutrophil-mediated inflammation in a target tissue in a subject in need thereof. In other embodiments, the compounds of Formulas I and IA, in combination with one or more compounds (e.g., a compound that increases the level and/or activity of MRP1, or a compound that increases NAEs) will show a synergistic effect in this regard.

In some embodiments, the methods, compounds, and compositions of the present technology relate to the use of one or more of the cyclosporine A compounds of Formula I and IA to treat, ameliorate, or prevent inflammatory bowel disease (IBD), such as ulcerative colitis (UC), Crohn's disease (CD), and infectious/non-infectious enterocolitis. In other embodiments, the compounds of Formula I (including but not limited to Formula IA, BT-051, BT-090, BT122, BT123, BT125, and BT126) in combination with one or more compounds (e.g., a compound that increases the level and/or activity of MRP1, or a compound that increases NAEs) will show a synergistic effect in this regard.

In some embodiments, the methods and compostions of the present technology relate to the use of one or more of the compounds of Formula I to treat, ameliorate, or prevent infectious and non-infectious inflammatory lung conditions, including, but not limited to, pneumococcal infection, asthma, chronic obstructive pulmonary disease (COPD), and pulmonary fibrosis. In other embodiments, the cyclosporine A compounds in combination with one or more compounds (e.g., a compound that increases the level and/or activity of MRP1, or a compound that increases NAEs) will show a synergistic effect in this regard.

In some embodiments, the methods, compounds and compositions of the present technology relate to the use of one or more of the cyclosporine A compounds of Formula I to treat, ameliorate, or prevent inflammatory skin diseases including, but no limited to, dermatitis (eczema), rosacea, seborrheic dermatitis, and psoriasis. In other embodiments, the cyclosporine A compounds in combination with one or more compounds (e.g., a compound that increases the level and/or activity of MRP1, or a compound that increases NAEs) will show a synergistic effect in this regard.

The methods of the present technology are useful for treating "inflammation," which is a localized physical condition in which part of the body reacts to injury and/or infection. The classic symptoms of inflammation are heat, redness, swelling, pain, and/or loss of function. These are manifestations of the physiologic changes that occur during the inflammatory process. The three major components of this process are: (1) changes in the caliber of blood vessels and the rate of blood flow through them (hemodynamic changes); (2) increased capillary permeability; and (3) leukocytic exudation. "Neutrophil-mediated inflammation" refers to the leukocytic exudation and stage of inflammation, in which neutrophils move to the endothelial lining of the small blood vessels (margination) and line the endothelium in a tightly packed formation (pavementing). Eventually, these neutrophils move through the endothelial spaces and escape into the extravascular space (emigration). Once they are outside the blood vessels they are free to move and, by chemotaxis, are drawn to the site of injury. Accumulations of neutrophils (and macrophages) at the area of inflammation act to neutralize foreign particles by phagocytosis.

Inflammation includes acute inflammation, which is usually of sudden onset, marked by the classical signs of heat, redness, swelling, pain, and loss of function, and in which vascular and exudative processes predominate; catarrhal inflammation, which is a form affecting mainly a mucous surface, marked by a copious discharge of mucus and epithelial debris; chronic inflammation, which is prolonged and persistent inflammation marked chiefly by new connective tissue formation; it may be a continuation of an acute form or a prolonged low-grade form; interstitial inflammation, which is inflammation affecting chiefly the stroma of an organ; traumatic inflammation, which is one that follows a wound or injury; ulcerative inflammation, in which necrosis on or near the surface leads to loss of tissue and creation of a local defect (ulcer).

Inflammation may be infectious and/or non-infectious. "Infectious" inflammation refers to inflammation that is associated with and/or is caused by the invasion and multiplication of microorganisms such as bacteria, viruses, and parasites that are not normally present within the body. In contrast, "non-infectious" inflammation refers to inflammation that is not associated with and/or is not caused by the invasion and multiplication of microorganisms such as bacteria, viruses, and parasites that are not normally present within the body.

In another embodiment, the present technology provides a method for treating neutrophil-mediated inflammation by targeting the pro-inflammatory MRP2/HXA$_3$ pathway. In a particular embodiment, this method for treating neutrophil-mediated inflammation in a target tissue of a mammalian subject in need thereof, comprises administering to the subject a therapeutically effective amount of one or more first compound that inhibits the activity and/or level of one or more of multidrug resistance protein 2 (MRP2) and hepoxilin A3 (HXA$_3$) synthase, wherein the therapeutic amount of the first compound reduces migration of neutrophils into the target tissue. In some embodiments, the compound is a cyclosporine A conjugate or precursor, such as a compound of Formula I (including but not limited to Formula IA, BT-051, BT-090, BT122, BT123, BT125, and BT126).

In various embodiments, suitable in vitro or in vivo assays are performed to determine the effect of a specific composition of the present technology and whether its administration is indicated for treatment. In various embodiments, in vitro assays can be performed with representative cell-based assays, such as the neutrophil migration assay. In other embodiments, in vivo models, typified by animal models, may be used to determine if a given cyclosporine A conjugate (or precursor) alone or in combination with one or more additional compounds (e.g., an additional compound that inhibit is one or more of MRP2 nd HXA$_3$ synthase, a compound that increases the level and/or activity of MRP1, or a compound that increases NAEs), exerts the desired effect in treating a disease or condition. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

In some embodiments, the methods of the present technology further comprise administering one or more antibiotic and/or anti-inflammatory agent. Examples of antibiotic/anti-inflammatory agents used singly or in combination in the methods of the present technology include, but are not limited to Dalbavancin (DALVANCE©, XYDALBA©), Oritavancin (ORBACTIVE©) Daptomycin (Cubicin©), Tedizolid (SIVEXTRO©), Ceftobiprole (ZEVTERA©, MABELIO©), Ceftolozane-tazobactam (ZERBAXA©) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the methods of the present technology further comprise administering one or more antibodies, such antibodies targeting one or more of *Clostridium difficile* toxins, tumor necrosis factor (TNF), interleukins, metalloproteinase-9 (such as the antibody GS-5745, Gilead).

For example, in Crohn's disease, it may be desirable that any one of the methods of the present technology further comprise administering one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia, UCB)), the anti-alpha-4 beta-7 integrin antibody vedolizumab (Entyvio, Takeda), the JAK inhibitors ABT-494 (AbbVie), and filgotinib (GLPG0634, Galapagos and Gilead) (Sandborn, The Present and Future of Inflammatory Bowel Disease Treatment Gastroenterology & Hepatology, Volume 12, Issue 7, July 2016).

For ulcerative colitis, it may be desirable that any one of the methods of the present technology further comprise administering one or more of 5-aminosalycylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead)) (Sandborn 2016).

V. Combination Therapies

In some embodiments, the cyclosporine A compounds of the present technology may be combined with one or more additional therapeutic agents for the prevention, amelioration, or treatment of a disease or condition.

In one embodiment, an additional therapeutic agent is administered to a subject in combination with a cyclosporine A conjugate or precursor of the present technology (e.g., a compound of Formula I, including but not limited to Formula IA, BT-051, BT-090, BT122, BT123, BT125, and BT126) such that a synergistic therapeutic effect is produced.

In some embodiments, the cyclosporine A compounds of the present technology (e.g., a compound of Formula I, including but not limited to Formula IA, BT-051, BT-090, BT122, BT123, BT125, and BT126) are combined with one or more methods or compounds for the treatment or prevention of celiac disease or symptoms associated with celiac disease. In some embodiments, the one or more compounds comprises an anti-inflammatory agent. In some embodiments, the one or more compounds comprises infliximab. In some embodiments, one or more methods comprises a gluten-free diet.

In some embodiments, the cyclosporine A compounds of the present technology (e.g., a compound of Formula I, including but not limited to Formula IA, BT-051, BT-090, BT122, BT123, BT125, and BT126) are combined with one or more compounds that increase levels of multidrug resistance protein 1 (MRP1) described above.

In some embodiments, the cyclosporine A compounds of the present technology (e.g., a compound of Formula I, including but not limited to Formula IA, BT-051, BT-090, BT122, BT123, BT125, and BT126) are combined with one or more additional compounds that inhibit one or more of multidrug resistance protein 2 (MRP2) and hepoxilin A3 (HXA$_3$) synthase described above.

In some embodiments, the cyclosporine A compounds of the present technology (e.g., a compound of Formula I, including but not limited to Formula IA, BT-051, BT-090, BT122, BT123, BT125, and BT126) are combined with one or more additional compounds that increase N-acylethanolamines (NAEs) described above.

In some embodiments, the cyclosporine A compounds of the present technology (e.g., a compound of Formula I, including but not limited to Formula IA, BT-051, BT-090, BT122, BT123, BT125, and BT126) are combined with one or more additional therapeutic agents for treating neutrophil-mediated inflammation and conditions associated therewith, including, but not limited to, ulcerative colitis and Crohn's disease. In some embodiments, the present technology provides compositions comprising one or more of a first compound that increases the level and/or activity of multidrug resistance protein 1 (MRP1), a second compound, such as a cyclosporine A conjugate, that inhibits one or more of multidrug resistance protein 2 (MRP2) and hepoxilin A3 (HXA$_3$) synthase, and/or a third compound that increases one or more N-acylethanolamines (NAEs).

The multiple therapeutic agents (e.g., cyclosporine A conjugates, compounds that increase the level and/or activity of MRP1, additional inhibitors of MRP2 and HXA$_3$ synthase, and/or compounds that increase NAEs) may be administered in any order or even simultaneously. If simultaneously, the multiple therapeutic agents may be provided in a single, unified form, or in multiple forms (by way of example only, either as a single formulation or as two separate formulations). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

In some embodiments, the methods of the present technology further comprise administering to the subject a therapeutically effective amount of at least one compound that increases the level and/or activity of one or more N-acylethanolamines (NAEs), wherein the therapeutic amount of the compound reduces migration of neutrophils into the target tissue.

In some embodiments, the compound that increases NAEs is a cannabinoid receptor type 2 (CB2) "agonist" (i.e., a compound that specifically binds to, and activates, CB2). CB2 agonists are exemplified by GW-405,833; AM-1241; HU-308; JWH-015; JWH-133; L-759,633; L-759,656; beta-caryophyllene; arachidonylcyclopropylamide; and arachidonyl-2'-chloroethylamide.

In some embodiments, the methods of the present technology may further comprise administering one or more antibiotic and/or anti-inflammatory agent. Examples of antibiotic/anti-inflammatory agents used singly or in combination in the methods of the present technology include, but are not limited to Dalbavancin (DALVANCE©, XYDALBA©), Oritavancin (ORBACTIVE©) Daptomycin (Cubicin©), Tedizolid (SIVEXTRO©), Ceftobiprole (ZEVTERA©, MABELIO©), Ceftobiprole (ZEVTERA©, MABELIO©), Ceftolozane-tazobactam (ZERBAXA©) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometholone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the methods of the present technology may further comprise administering one or more antibodies, such as antibodies targeting one or more of *Clostridium difficile* toxins, tumor necrosis factor (TNF), interleukins, metalloproteinase-9 (such as the antibody GS-5745, Gilead).

In some embodiments, the present disclosure encompasses methods for the treatment, amelioration, or prevention of Crohn's disease, comprising administering one or more compounds of the present technology in combination with at least one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia, UCB)), the anti-alpha-4 beta-7 integrin antibody vedolizumab (Entyvio, Takeda), the JAK inhibitors ABT-494 (AbbVie), and filgotinib (GLPG0634, Galapagos and Gilead) (Sandborn, *Gastroenterology* & *Hepatology* 12(7) (2016)).

In some embodiments, the present disclosure encompasses methods for the treatment, amelioration, or prevention of ulcerative colitis, comprising administering one or more compounds of the present technology in combination with at least one or more of 5-aminosalycylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead)) (Sandborn, 2016).

VI. Modes of Administration

Any method known to those in the art for contacting a cell, organ, or tissue with compounds of the present technology may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of a compound of the present technology to a mammal such as a human. When used in vivo for therapy, a compound of the present technology is administered to a mammal in an amount effective to obtain the desired result, e.g., of treating the mammal. The effective amount is determined during pre-clinical trials and clinical trials by methods familiar to physicians and clinicians. The dose and dosage regimen will depend upon the degree of the disease or condition in the subject, the characteristics of the particular compound of the present technology used, e.g., its therapeutic index, the subject, and the subject's history.

An effective amount of a compound of the present technology useful in the present methods, such as in a pharmaceutical composition or medicament, may be administered to a mammal in need thereof by any of a number of well-known methods for administering pharmaceutical compositions or medicaments. The compounds of the present technology may be administered systemically or locally.

The compounds of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

In some embodiments, the pharmaceutical compositions of the present disclosure contain a pharmaceutically acceptable carrier and/or excipient suitable for rendering the compound or mixture administrable orally as a tablet, capsule or pill, or parenterally, intravenously, intradermally, intramuscularly or subcutaneously, or transdermally.

Pharmaceutical compositions are typically formulated to be compatible with the intended route of administration. Administering the pharmaceutical composition of the present disclosure may be accomplished by any means known to the skilled artisan. Routes of administration include, but are not limited to, parenteral, intravenous, intramuscular, intradermal, intraperitoneal, intratracheal, subcutaneous, oral, intranasal/respiratory (e.g., inhalation), transdermal (topical), sublingual, ocular, vaginal, rectal, and transmucosal administration. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In some embodiments, administration is topical and/or at the luminal surface of the tissue to be treated. "Topical" administration of a composition means contacting the composition with the skin. "Luminal surface" refers to the inner open space or cavity of a tubular organ, such as the interior central space in an artery or vein through which blood flows; the interior of the gastrointestinal tract; the pathways of the bronchi in the lungs; the interior of renal tubules and urinary collecting ducts; the pathways of the female genital tract, starting with a single pathway of the vagina, splitting up in two lumina in the uterus, both of which continue through the fallopian tubes.

In some embodiments, the compounds of the present technology are administered topically and/or at a luminal surface of the target tissue. This is advantageous to reduce potential systemic toxic side effects of the compounds.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EXPERIMENTAL EXAMPLES

The present technology is further illustrated by the following examples, which should not be construed as limiting in any way.

Example 1: Synthesis of PEG-Cyclosporine a Conjugates

Illustrative examples of the general synthesis of PEG-cyclosporine A conjugates is shown in Schemes 1 and 2. As will be understood by those of skill in the art, the side chain to which PEG is attached may be varied in length by using suitable homologs of olefinic ester, 1. For example, benzyl pent-4-enoate may be substituted with benzyl prop-2-enoate (benzyl acrylate), benzyl but-3-enoate, benzyl hex-5-enoate, or benzyl hept-6-enoate to provide a shorter or longer side chain. The use of such homologs is within the skill in the art.

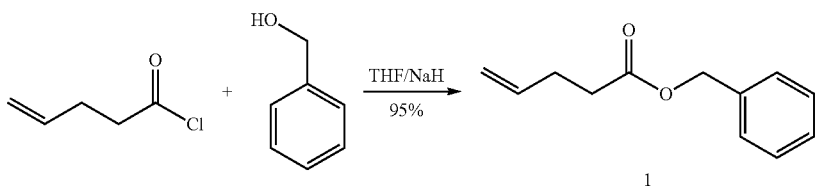

Scheme 1

-continued
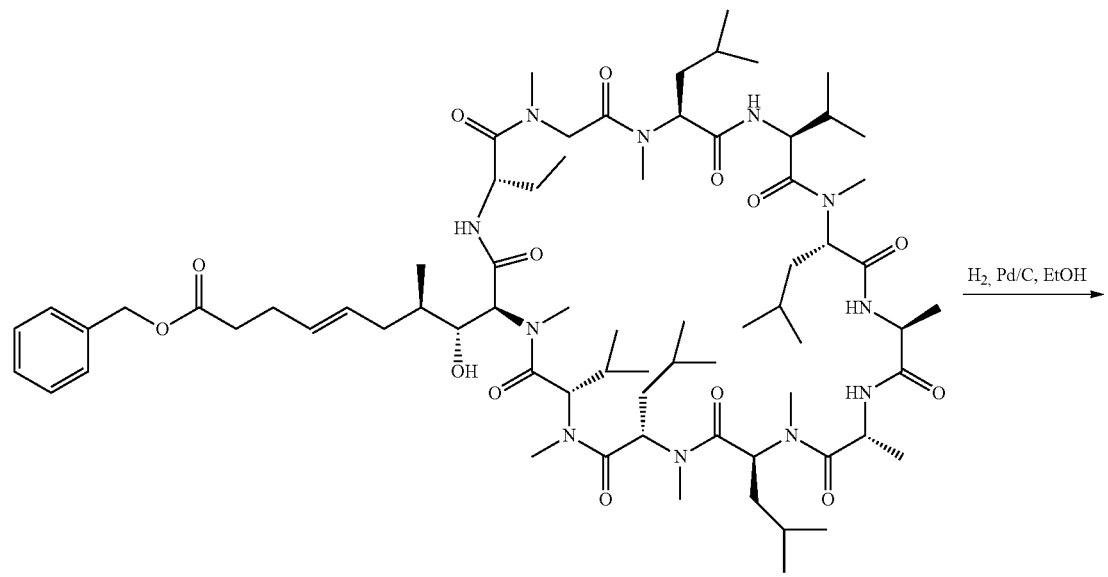
3
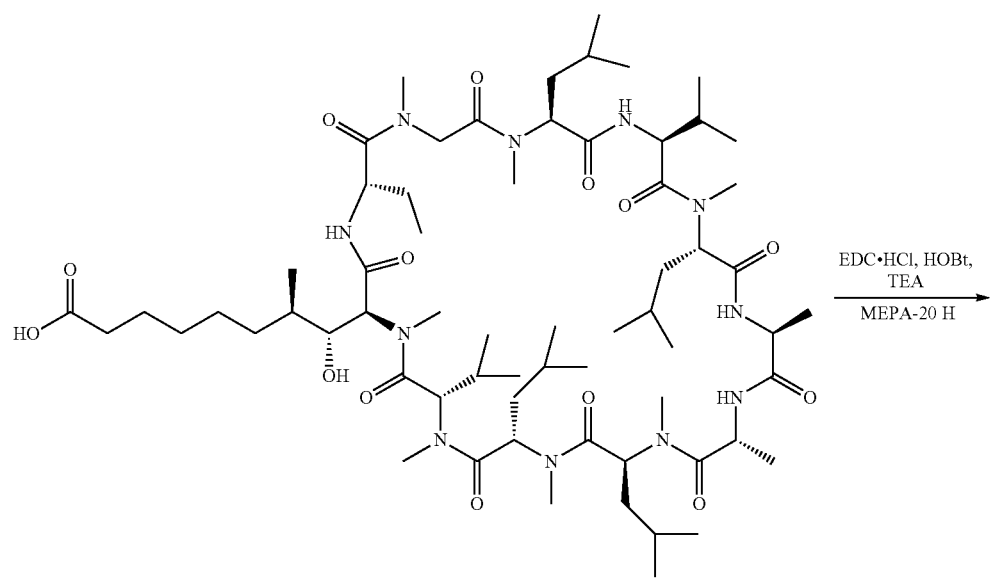
4

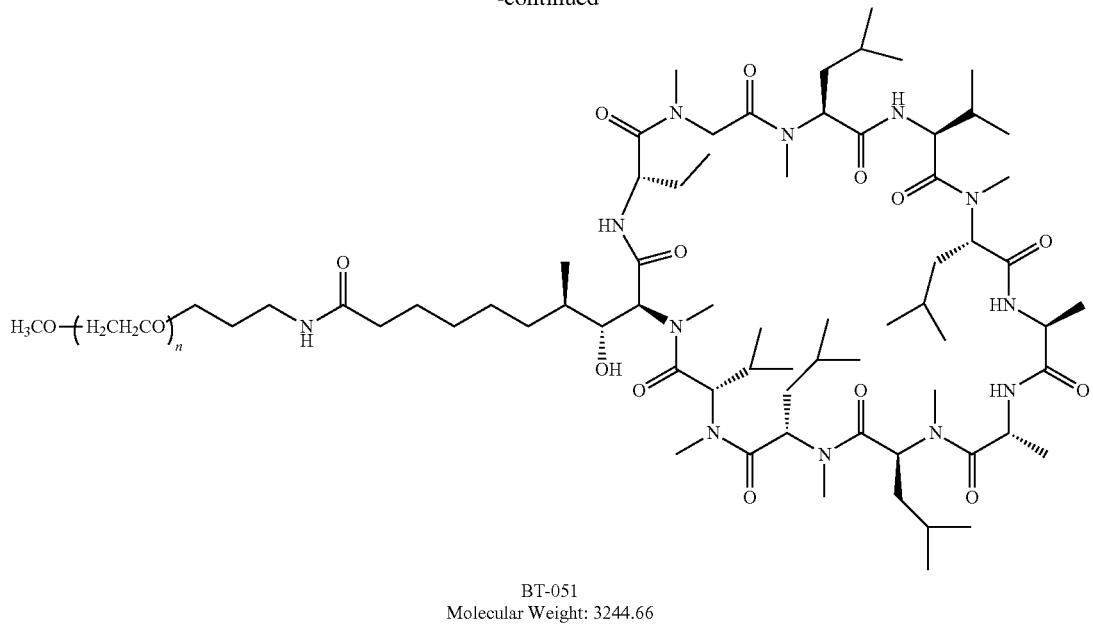

BT-051
Molecular Weight: 3244.66

Synthesis of Intermediate 1. A 2 L round bottom flask equipped with a mechanical stirrer and a thermocouple was purged with nitrogen. Sodium hydride (18.9 g, 1.05 eq, 60% dispersion in mineral oil, Sigma) followed by anhydrous THF (540 mL, 10 vol, Sigma) was added. The mixture was cooled to <10° C. in an ice-water bath. Then, benzyl alcohol (50.9 mL, 0.473 mol, 1.05 eq, Sigma) was added dropwise over a period of 45 min. The internal temperature was maintained at <10° C. during the addition. The ice bath was removed and the reaction mixture was warmed to ambient temperature and was stirred for 15 min. The mixture was again cooled to <10° C. 4-pentenoyl chloride (50 mL, 1 eq, 0.450 mol, Sigma) was added dropwise over a period of 60 min (internal temperature went from 5 to 15° C. during the addition). The reaction was warmed to ambient temperature and was stirred for 20 h. The reaction was quenched with 30 mL sat. $NH_4Cl$ and EtOAc (250 mL) was added. The layers were separated and organic layer was washed with sat. $NaHCO_3$(200 mL), and then brine (200 mL). The organic layer was dried over anhydrous $Na_2SO_4$, filtered and the filtrate was concentrated by rotary evaporation to obtain crude 1 as an oil. The crude was purified by chromatography ($SiO_2$, 1 kg, 25 cm×10 cm, 10% EtOAc/heptanes) to give intermediate 1 (81.9 g, 95% yield) as a clear liquid. The $^1H$ NMR was consistent with the assigned structure and the HPLC purity was 98.9%.

Synthesis of Intermediate 3. A 25 mL round bottomed flask equipped with a magnetic stir bar was placed under a blanket of nitrogen. Compound 2 (1.40 g, 1.16 mmol, 1.0 eq) followed by DCM (35 mL, degassed by nitrogen purging) was added resulting in a solution. To this was added intermediate 1 (1.87 g, 9.84 mmol, 8.5 eq). This mixture was degassed by nitrogen purging for 5 min. The flask was then charged with Grubb's $2^{nd}$ generation catalyst (0.11 g, 0.13 mmol, 0.13 eq, Sigma-Aldrich), and the mixture was again degassed with nitrogen purging for 5 min. The mixture was brought to reflux under argon with vigorous stirring for 17 h. The reaction mixture was cooled to ambient temperature and was evaporated to dryness. The residue was purified by chromatography (ISCO, $SiO_2$, 0-10% MeOH/DCM) to give intermediate 3 (1.1 g) as a light yellow solid, which contains 7.3% of compound 2 as determined by HPLC analysis.

The reaction was repeated on 5 g scale (compound 2) under the same conditions. The crude that was obtained will be purified by column chromatography.

Synthesis of Intermediate 4 (BT-070). A 150 mL Fisher Porter bottle was charged with intermediate 3 (1.0 g, 0.74 mmol, 1.0 eq), 10% Pd/C (0.40 g, 50% water, Johnson Matthey), and EtOH (20 mL). The flask was evacuated by vacuum and refilled with $H_2$ three times and was stirred under 50 PSI of hydrogen pressure for 23 h. The reaction mixture was filtered through a pad of Celite and the pad was washed with methanol (2×10 mL). The combined filtrate was concentrated by rotary evaporation to give intermediate 4 as a solid (0.95 g). As used herein, intermediate 4 of Scheme 1 also refers to BT-070.

Synthesis of BT-051. A nitrogen flushed 50 mL R.B. flask equipped with a magnetic stir bar was charged with crude intermediate 4 (0.57, AMRI, JWU-B-5-1), MEPA-20H (1.00 g, NOF), HOBt·$H_2O$ (0.096 g, Aldrich). The mixture was placed under a blanket of $N_2$, and was dissolved in acetonitrile (10 mL, Sigma Aldrich). TEA (0.18 mL) was added and the mixture was cooled in an ice-water bath. EDC·HCl (0.104 g, Sigma-Aldrich) was added in a single portion, and the reaction was removed from the ice bath and allowed to gradually warm to ambient temperature. The reaction was judged complete by HPLC analysis after 21 h. The reaction was diluted with DCM (50 mL) and was washed with DI $H_2O$ (2×20 mL) and brine (20 mL). The organic layer was dried over anhydrous $Na_2SO_4$, filtered and the filtrate was concentrated under reduced pressure. The crude material was purified by chromatography ($SiO_2$, 5-15% MeOH/DCM) to give BT-051 as a white solid (0.40 g, 27% yield). The $^1H$ NMR was consistent with the assigned structure and the HPLC purity was 98.2%.

The general synthesis of PEG-cyclosporine A conjugates as shown in Scheme 1 also led to the production of +/−CH$_2$ derivatives of BT-070 and BT-051, which are shown below. Without wishing to be bound by theory, it is believed that the +/−CH$_2$ derivatives were generated by Scheme 1 due to the use of Grubb's catalyst in the first step of the synthesis, which encourages double bond migration. The derivative of BT-070 having one additional carbon in the linker (L$_1$=—CH$_2$CH$_2$CH$_2$—) is BT125. The derivative of BT-070 having one fewer carbon in the linker (L$_1$=—CH$_2$—) is BT122. The derivative of BT-051 having one additional carbon in the linker (L$_1$=—CH$_2$CH$_2$CH$_2$—) is BT126. The derivative having one fewer carbon in the linker (L$_1$=—CH$_2$—) is BT123.

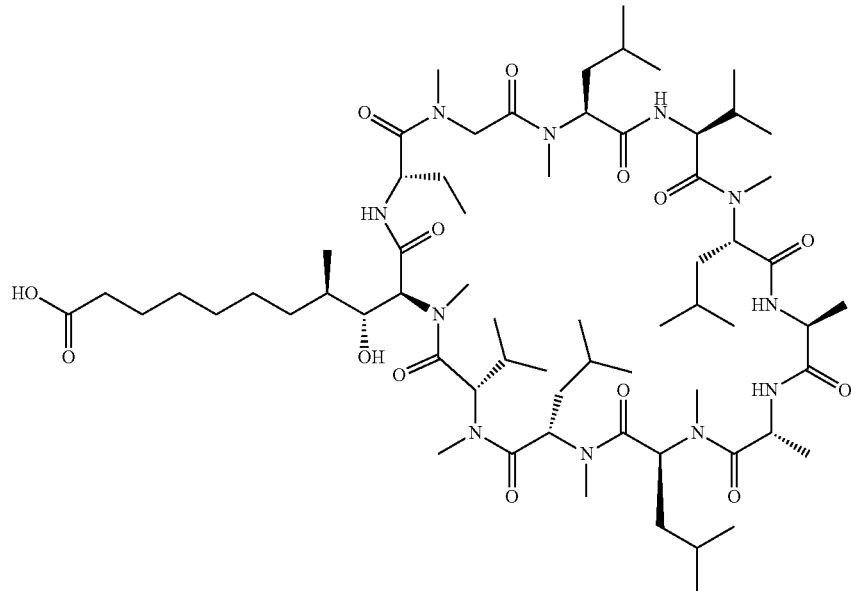

BT125

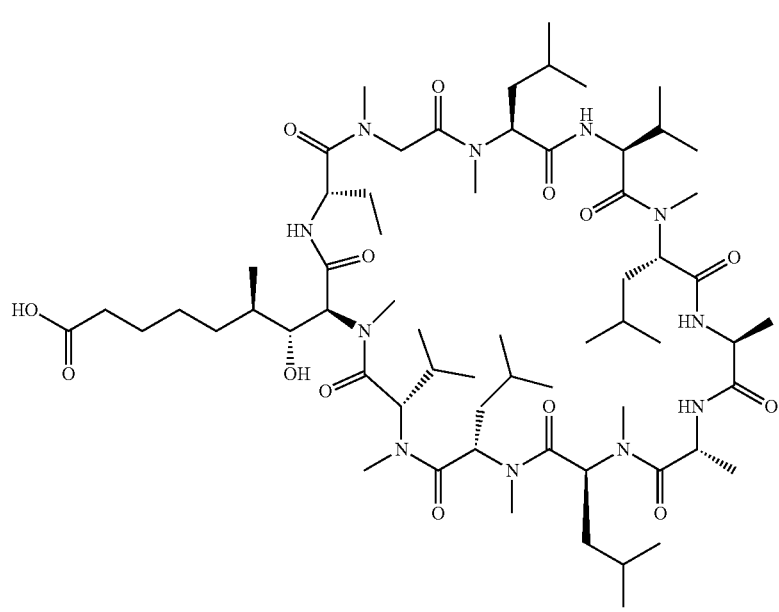

BT122

-continued
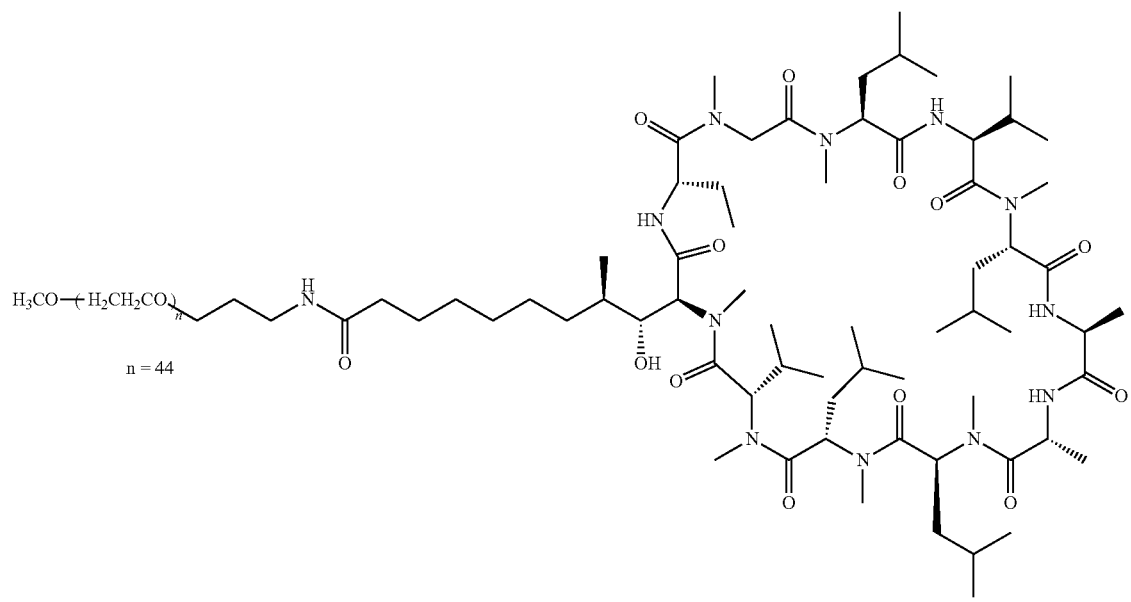
BT126
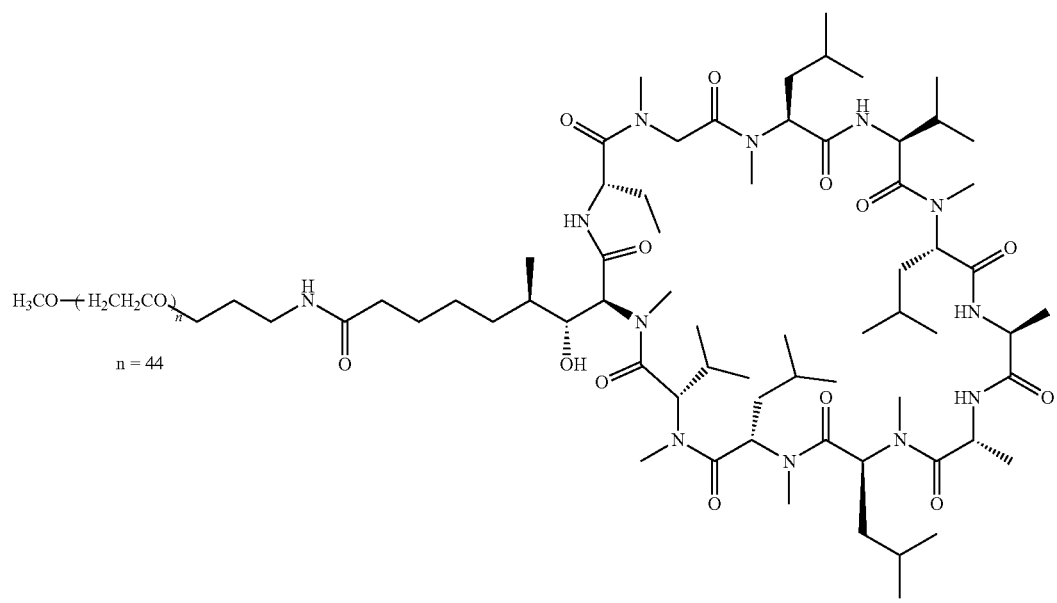
BT123
Scheme 2
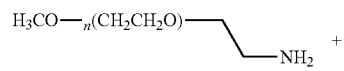
PLS-269

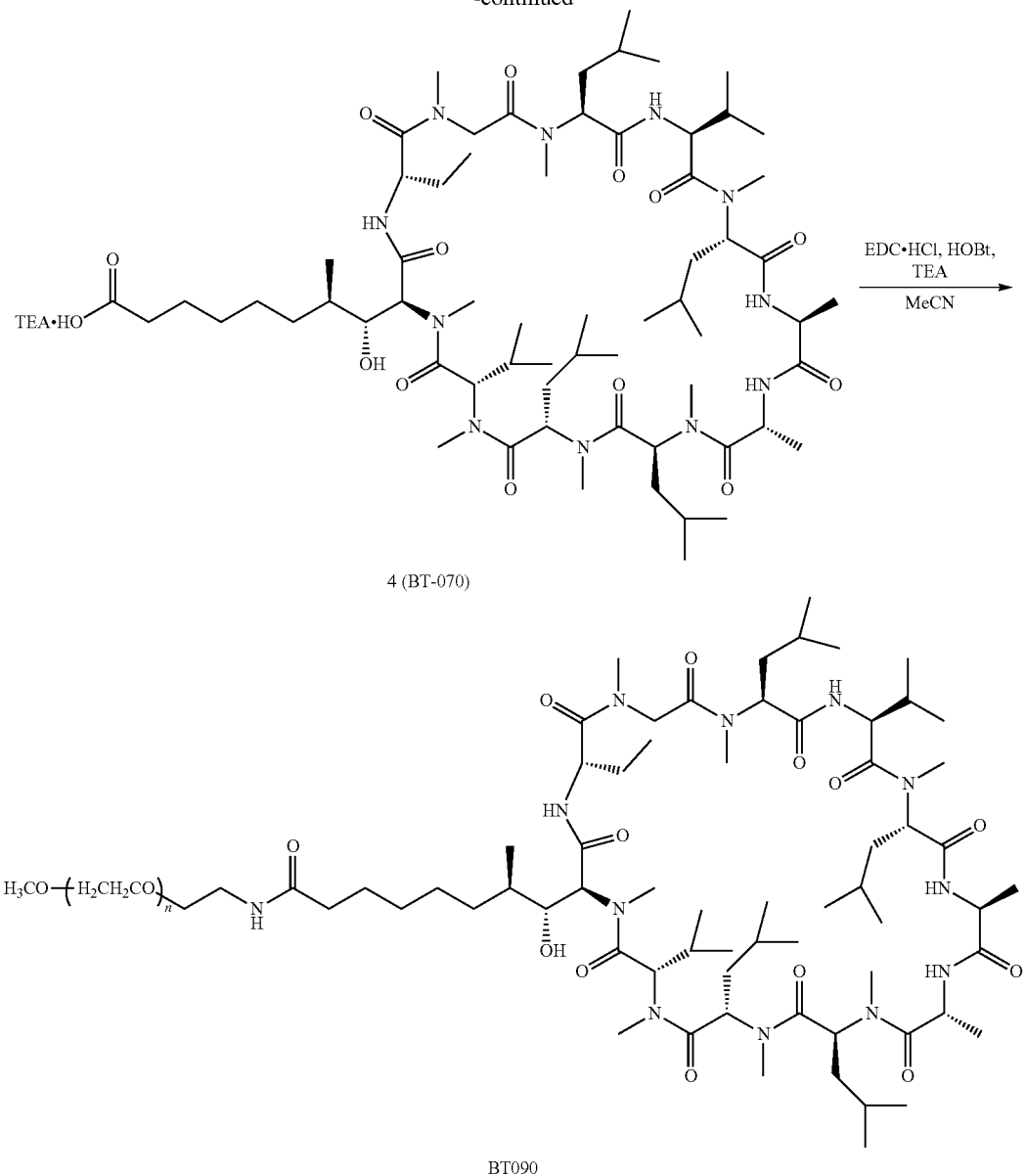

4 (BT-070)

BT090

Synthesis of BT-090. Reaction conditions: 1.0 eq CsA acid (BT070, aka Intermediate 4), 1.25 eq PLS-269, 1.4 eq EDC·HCl, 1.25 eq HOBt, 1 eq TEA, MeCN (4 mL, 31.7 vol), 0° C.-rt, 28.5 h (Scheme 2). To a 100 mL R.B. containing HOU-E-63-3 (0.126 g, AMRI) was charged IMEPA-20H (0.230 g, NOF), HOBt·H$_2$O (0.019 g, Aldrich), and a stir bar. The reagents were placed under a blanket of N$_2$, dissolved in acetonitrile (3.2 mL, Sigma Aldrich) then TEA (0.013 mL, Aldrich), and were placed in an ice bath with stirring for 10 min EDC·HCl (0.027 g, Sigma-Aldrich) was added in a single portion, and the reaction was removed from the ice bath and allowed to gradually warm to room temperature. After 21 h, the reaction was diluted with DCM (50 mL, Pride) and was extracted with DI H$_2$O (2×20 mL), brine (20 mL), dried over Na$_2$SO$_4$, and concentrated under reduced pressure. The crude material was purified by chromatography (SiO$_2$, 5-15% MeOH/DCM) to give product (0.181 g, 61%). The material was dissolved in a minimal amount water, frozen evenly in a dry ice/acetone bath, and lyophilized until dry to give a white solid.

Example 2: Inhibition of Neutrophil Migration by Compounds of the Present Technology This example demonstrates the efficacy of the compounds of the present technology in inhibiting neutrophil migration in vitro, and that the compounds of the present technology exhibit a dose-responsive inhibition of neutrophil migration.

PMN transmigration assay. T84 colorectal cancer cells were grown to confluence on the bottom side of 12 well polycarbonate membrane inserts of a 24 well Transwell® plate. The confluent growth of these epithelial cells results in physiologically-relevant apical (luminal) and basolateral surfaces in the transwells.

The apical surface of the monolayer was treated with BT051, BT070, BT090, BT122, BT123, BT125, or BT126 over a dose range for 1 hour. The monolayer was then infected on the apical surface with *Salmonella typhimurium* for 2 hours to induce hepoxilin A3 ($HXA_3$) efflux through the MRP2 membrane protein and into the apical chamber.

The bacteria were washed off the monolayer and the apical surface re-exposed to BT051, BT070, BT090, BT122, BT123, BT125, or BT126. Freshly isolated and prepared human neutrophils were then added to the basolateral side and allowed to transmigrate through the monolayer for 2 hours. The number of neutrophils migrated to the apical chamber (due to the $HXA_3$ gradient) was then assayed by determination of myeloperoxidase activity (a neutrophil biomarker). Inhibition of transmigration is indicated by lower MPO activity in the apical chamber.

Results. As shown in FIG. 1, BT051 and BT070 exhibit dose-responsive inhibition of neutrophil migration. A 50% inhibition was observed at compound concentrations of 31.25 nM.

As shown in Table A, BT051 and BT070 exhibit inhibition of neutrophil migration at a dose of 100 nM. However, BT090 does not exhibit inhibition of neutrophil migration at a dose of 100 nM. For the purpose of Table A, the PEG-cyclosporine A conjugate/precursor is represented by the compound having the following formula: (IA).

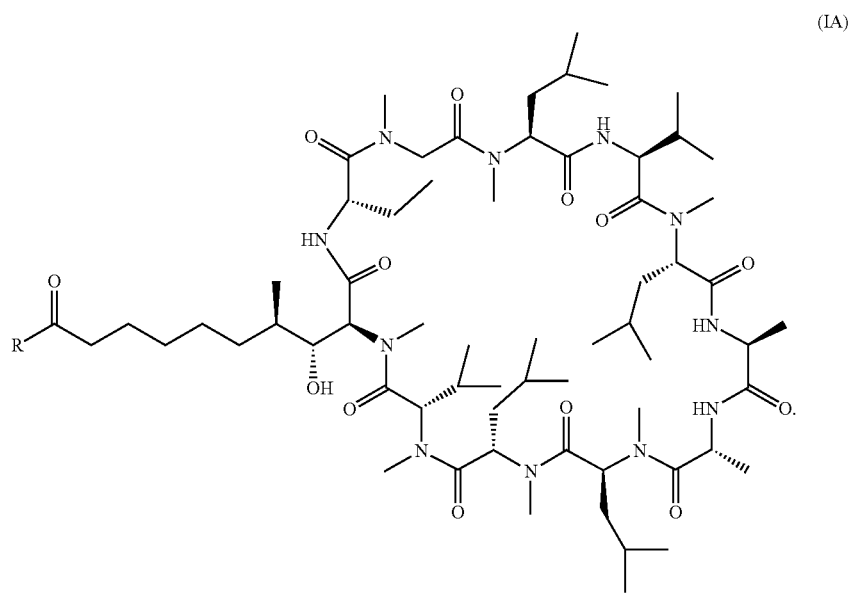

(IA)

TABLE A

Inhibitory activity of PEG-cyclosporine A conjugates and precursors in the neutrophil transmigration assay (compounds tested at 100 nM).

| Compound | R= | % Inhibition |
|---|---|---|
| BT051 | $CH_3O—(CH_2\ CH_2O)_{44}—CH_2CH_2CH_2NH—$ | 50 |
| BT090 | $CH_3O—(CH_2\ CH_2O)_{44}—CH_2CH_2NH—$ | 0 |
| BT070 | HO— | 50 |

As shown in Table B, derivatives of BT051 having one additional carbon in the linker (BT126) or one fewer carbon in the linker (BT123), and derivatives of BT070 having one additional carbon in the linker (BT125) or one fewer carbon in the linker (BT122) exhibit inhibition of neutrophil migration at a dose of 100 nM. For the purpose of Table B, the PEG-cyclosporine A conjugate/precursor is represented by the compound having the following formula.

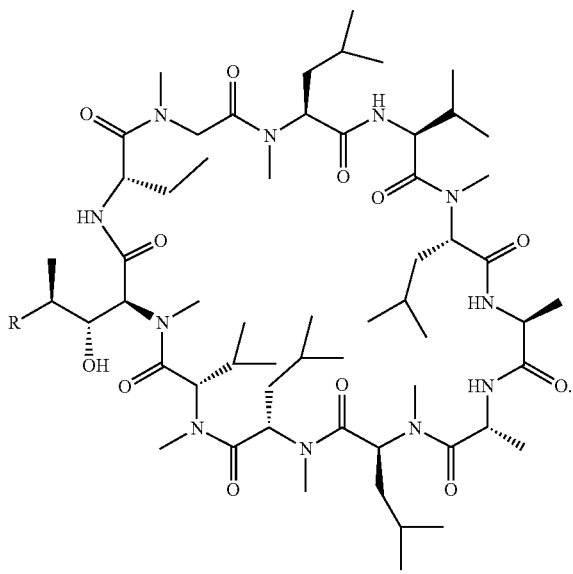

(IB)

TABLE B

Inhibitory activity of PEG-cyclosporine A conjugates and precursors in the neutrophil transmigration assay (compound tested at 100 nM).

| Compound | R= | % Inhibition |
|---|---|---|
| BT122 | COOH—$CH_2CH_2CH_2CH_2$— | 25 |
| BT123 | $CH_3O$—$(CH_2CH_2O)_{44}$—$CH_2CH_2CH_2NH$—CO—$CH_2CH_2CH_2CH_2$— | 50 |
| BT125 | COOH—$CH_2CH_2CH_2CH_2CH_2CH_2$— | 95 |
| BT126 | $CH_3O$—$(CH_2CH_2O)_{44}$—$CH_2CH_2CH_2NH$—CO—$CH_2CH_2CH_2CH_2CH_2CH_2$— | 50 |

These results demonstrate the surprising and unexpected capability of certain PEG-cyclosporine A conjugates/precursors to inhibit neutrophil migration. Accordingly, these results demonstrate that compounds of the current technology are useful in methods for inhibiting neutrophil migration, such as methods for the prevention or treatment of diseases or conditions caused by, resulting in, or otherwise associated with neutrophil migration.

Example 3: Stability of PEG-Cyclosporine a Compounds in Simulated Intestinal Fluid, Simulated Gastric Fluid, and Feces This example demonstrates that the PEG-Cyclosporine A compounds (including conjugates) of the present technology are stable in simulated intestinal fluid, simulated gastric fluid, and feces.

A. BT090

Feces stability. Immediately prior to the study, male Sprague-Dawley rat feces were collected overnight over a mix of dry and wet ice. Feces were then homogenized in phosphate buffer at pH 6.5 and filtered to remove particles. BT090 (10 μm) was incubated in duplicate at 37° C. for a total of 24 hours in the freshly prepared rat feces homogenate. At selected time points (0.5, 2, 6 and 24 hours), a 25 μL aliquot was taken from the incubation mixtures and quenched with 225 μL of acetonitrile containing the internal standards (IS). Samples were then centrifuged to pellet the precipitated proteins and the supernatants were diluted 5-fold. The 0 hour samples were prepared in pre-quenched feces homogenate towards the end of the incubation period. All quenched samples were then submitted to bioanalysis for LC-MS/MS quantification.

SGF/FeSSIF Stability Procedure. BT090 (10 μM) was incubated in duplicate at 37° C. for a total of 6 hours in simulated gastric fluid (SGF) (Ricca, Arlington, Tex.) and Fed State Simulated Intestinal Fluid (FeSSIF) (Biorelevant, London, UK). The reactions were initiated by spiking the test articles (1 mM water stock solutions) in their respective buffers. At selected time points (0, 0.5, 1, 2, 4, and 6 hours), a 50 μL aliquot was taken from the incubation mixtures and frozen at −80° C. At the end of the incubation period, 200 μL of 50:50 acetonitrile:water containing the internal standards (IS) were added to every tube and vortexed thoroughly. The 0 hour samples were prepared in pre-quenched SGF or FeSSIF. All quenched samples were then submitted to bioanalysis for LC-MS/MS quantification.

Bioanalysis. BT090 samples were analyzed by LC-MS/MS using a Thermo Accela UPLC and a Thermo Q-Exactive mass spectrometer. The [M+H]+ adducts of the compounds and internal standards were monitored using positive mode electrospray ionization in exact mass mode. The analytes were injected onto a C18 column and chromatographed using a reverse phase gradient with 0.1% formic acid in water and 0.1% formic acid in 20/80 isopropyl alcohol/acetonitrile mobile phases. Since there are several species in the polymeric mixture, the 5 most prominent peaks were integrated (masses tracked: 768.8, 779.8, 792.0, 801.8, 813.0; all 4+ charge state)

Figure 2A:
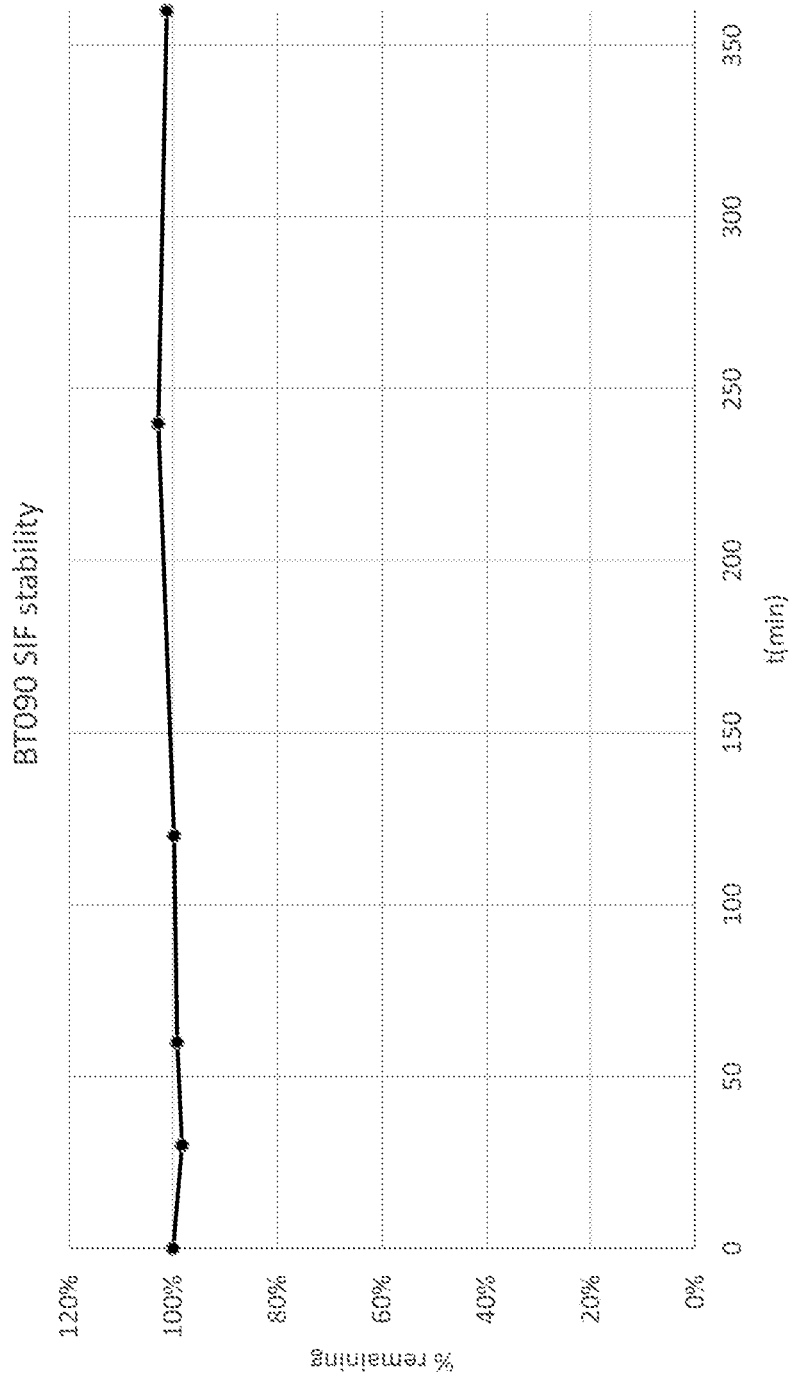
FIGS. 2A, 2B, and 2C.
Figure 2B:
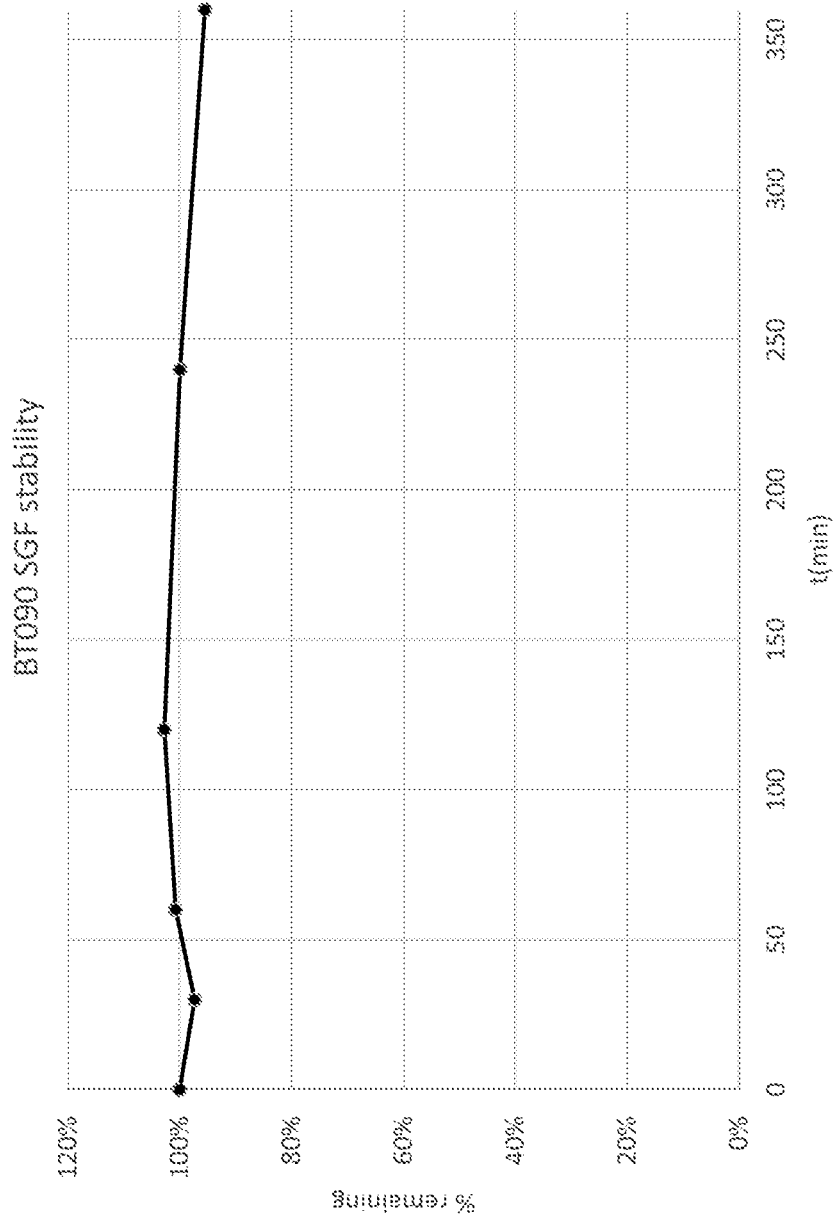
Figure 2C:
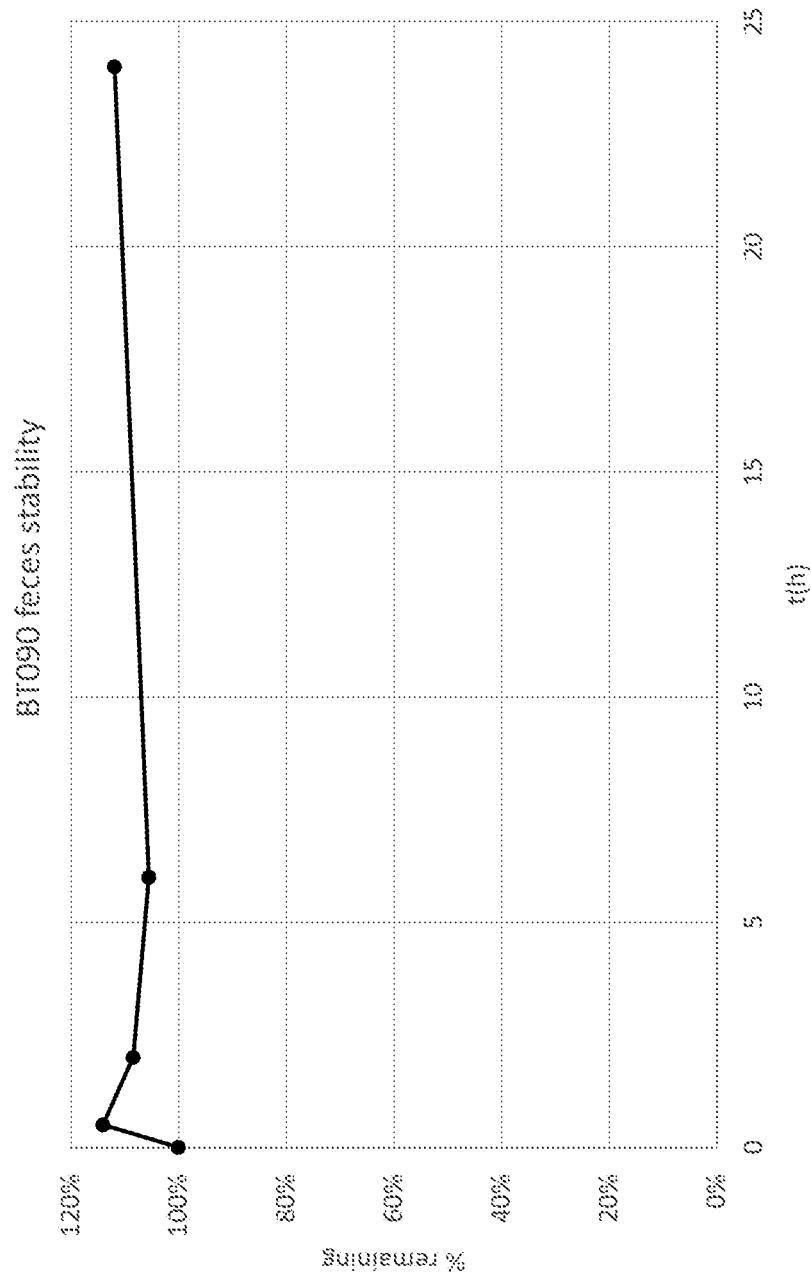

Results. As shown in FIG. 2A, BT090 is stable in simulated intestinal fluid. The compound was incubated for over 6 hours in FeSSIF and assayed for compound remaining at the time points indicated. As shown in FIG. 2B, BT090 is stable in simulated gastric fluid. The compound was incubated over 6 hours in SGF and assayed for compound remaining at the time points indicated. As shown in FIG. 2C, BT090 is stable in fresh rat fecal homogenate. The compound was incubated over 24 hours in feces and assayed for compound remaining at the time points indicated.

B. BT051 and BT070

Feces stability. Immediately prior to the study, male Sprague-Dawley rat feces are collected overnight over a mix of dry and wet ice. Feces are then homogenized in phosphate buffer at pH 6.5 and filtered to remove particles. BT051 and BT070 (10 PM) are incubated in duplicate at 37° C. for a total of 24 hours in the freshly prepared rat feces homogenate. At selected time points (0.5, 2, 6 and 24 hours), a 25 μL aliquot is taken from the incubation mixtures and quenched with 225 L of acetonitrile containing the internal standards (IS). Samples are then centrifuged to pellet the precipitated proteins and the supernatants are diluted 5-fold. The 0 hour samples are prepared in pre-quenched feces homogenate towards the end of the incubation period. All quenched samples are then submitted to bioanalysis for LC-MS/MS quantification.

SGF/FeSSIF Stability Procedure. BT051 and BT070 (10 μM) are incubated in duplicate at 37° C. for a total of 6 hours in simulated gastric fluid (SGF) (Ricca, Arlington, Tex.) and Fed State Simulated Intestinal Fluid (FeSSIF) (Biorelevant, London, UK). The reactions are initiated by spiking the test articles (1 mM water stock solutions) in their respective buffers. At selected time points (0, 0.5, 1, 2, 4, and 6 hours), a 50 μL aliquot is taken from the incubation mixtures and frozen at −80° C. At the end of the incubation period, 200 μL of 50:50 acetonitrile:water containing the internal standards (IS) are added to every tube and vortexed thoroughly. The 0 hour samples are prepared in pre-quenched SGF or FeSSIF. All quenched samples are then submitted to bioanalysis for LC-MS/MS quantification.

Bioanalysis. BT051 and BT070 samples are analyzed by LC-MS/MS using a Thermo Accela UPLC and a Thermo Q-Exactive mass spectrometer. The [M+H]+ adducts of the compounds and internal standards are monitored using positive mode electrospray ionization in exact mass mode. The analytes are injected onto a $C_{18}$ column and chromatographed using a reverse phase gradient with 0.1% formic acid in water and 0.1% formic acid in 20/80 isopropyl alcohol/acetonitrile mobile phases. Since there are several species in the polymeric mixture, the 5 most prominent peaks are integrated (masses tracked: 768.8, 779.8, 792.0, 801.8, 813.0; all 4+ charge state)

Results. It is predicted that BT051 and BT070 will be stable in simulated intestinal fluid, simulated gastric fluid, and fresh rat fecal homogenate.

These results show that compounds of the present technology are useful for methods comprising exposure of the compounds to intestinal fluid, gastric fluid, and fecal material, such as methods for the treatment of gastrointestinal disease.

Example 4: Pharmacokinetics of PEG-Cyclosporine a Compounds of the Present Technology This example demonstrates the pharmacokinetics of compounds of the present technology.

Three male, cannulated, fasted Sprague-Dawley rats were administered 10 mg/kg BT090, BT051, or BT070 orally at a dose rate of 10 mL/kg at t=0 h. Blood samples were collected at the indicated time points and processed to plasma. Plasma concentrations of BT090 were assayed by LC-MS/MS. Feces were collected over t=0 to 4 h, 4-8 h, and 8-24 h, homogenized in buffer and assayed for BT090 concentrations by LC-MS/MS. Total feces weight collected for each time interval was recorded. BT090 was formulated in 1% NMP, 0.3% Tween-80 in 0.5% methylcellulose.

Tables 1-4 show, respectively, the oral bioavailability of compounds BT090, BT051, BT070 (the breakdown product of orally dosed BT051), and BT070 (dosed separately). As shown in Table 1, BT090 is not orally bioavailable. BT090, when dosed orally in rats at 10 mg/kg, was not detectable in the plasma from 15 minutes to 24 hours. Only rat "C" showed any detectable level at 15 min, and this level was close to the limit of detection of the assay (25 ng/mL). NQ-below the limit of detection of the bioanalytical assay. NC—not calculated due to lack of data. As shown in Table 2, BT051 is orally bioavailable. BT051, when dosed orally in rats at 10 mg/kg, was detectable in the plasma at 15 minutes in each of the rat subjects (A-E). As shown in Table 3, the breakdown product of BT051 (i.e., BT070) is not orally bioavailable following oral administration of BT051 in rats at 10 mg/kg. As shown in Table 4, BT070, when dosed separately at 10 mg/kg orally in rats, is present in the plasma in all subject rats from 15 minutes to 24 hours.

TABLE 1

BT090 Rat PK.

| | Animal ID | | | Mean | SD | % |
|---|---|---|---|---|---|---|
| Time (h) | A | B | C | (ng/mL) | (ng/mL) | CV |
| 0.25 | NQ | NQ | 27.0 | 27.0 | — | — |
| 0.5 | NQ | NQ | NQ | — | — | — |
| 1 | NQ | NQ | NQ | — | — | — |
| 2 | NQ | NQ | NQ | — | — | — |
| 4 | NQ | NQ | NQ | — | — | — |
| 6 | NQ | NQ | NQ | — | — | — |
| 8 | NQ | NQ | NQ | — | — | — |
| 24 | NQ | NQ | NQ | — | — | — |
| $C_{max}$ (ng/mL) | NC | NC | 27.0 | 27.0 | — | — |
| $t_{max}$ (h) | NC | NC | 0.25 | 0.25 | — | — |
| $AUC_{last}$ (ng/mL * h) | NC | NC | NC | — | — | — |
| $AUC_{inf}$ (ng/mL * h) | NC | NC | NC | — | — | — |
| % Extrapolation | NC | NC | NC | — | — | — |
| CL_F (mL/min/kg) | NC | NC | NC | — | — | — |
| M.R.T. po (h) | NC | NC | NC | — | — | — |

NQ: Not quantifiable. No peak or below limit of quantification (LOQ = 25.0 ng/mL)
NC: Not calculated.

TABLE 2

BT051 Rat PK.

| | Animal ID | | | | | Mean | SD | |
|---|---|---|---|---|---|---|---|---|
| Time (h) | A | B | C | D | E | (ng/mL) | (ng/mL) | % CV |
| 0.25 | 22.5 | 35.2 | 35.7 | 42.5 | 23.1 | 31.8 | 8.7 | 27.4 |
| 0.5 | 28.3 | 56.2 | 38.1 | 14.4 | 26.6 | 32.7 | 15.6 | 47.6 |
| 1 | 16.0 | 51.5 | 28.4 | 13.3 | 18.9 | 25.6 | 15.5 | 60.6 |
| 2 | 11.1 | 34.1 | 12.8 | 10.7 | 11.3 | 16.0 | 10.2 | 63.5 |
| 4 | 9.2 | 17.3 | 10.2 | 24.5 | NQ | 15.3 | 7.1 | 46.4 |
| 6 | NQ | 7.7 | 8.7 | 21.6 | NQ | 12.7 | 7.7 | 60.9 |
| 8 | NQ | 7.0 | 7.4 | 8.4 | 62.7 | 21.4 | 27.5 | 128.8 |
| 24 | NQ | NQ | NQ | NQ | NQ | — | — | — |
| $C_{max}$ (ng/mL) | 28.3 | 56.2 | 38.1 | 42.5 | 62.7 | 45.6 | 13.8 | 30.4 |
| $t_{max}$ (h) | 0.50 | 0.50 | 0.50 | 0.25 | 8.00 | 1.95 | 3.38 | 173.53 |
| $AUC_{last}$ (ng/mL * h) | 54.2 | 176.8 | 109.0 | 142.6 | 257.4 | 148.0 | 76.1 | 51.4 |
| $AUC_{inf}$ (ng/mL * h) | 108.5* | 208.2 | 201.7* | 174.3 | 368.1* | 212.1 | 95.7 | 45.1 |
| % Extrapolation | 50.0 | 15.1 | 46.0 | 18.1 | 30.1 | 31.9 | 15.8 | 49.7 |
| CL_F (mL/min/kg) | 1535.8* | 800.5 | 826.4* | 956.4 | 452.8 | 914.4 | 394.2 | 43.1 |
| M.R.T. po (h) | 5.8* | 4.0 | 11.0* | 5.4 | 7.3* | 6.69 | 2.68 | 40.08 |

NQ: Not quantifiable. No peak or below limit of quantification (LOQ = 5.0 ng/mL)
NC: Not calculated.

TABLE 3

BT070 (breakdown product of BT051) Rat PK.

| Time (h) | \multicolumn{5}{c}{Animal ID} | Mean (ng/mL) | SD (ng/mL) | % CV |
|---|---|---|---|---|---|---|---|---|
| | A | B | C | D | E | | | |
| 0.25 | NQ | NQ | NQ | NQ | NQ | — | — | — |
| 0.5 | 3.3 | NQ | NQ | NQ | NQ | 3.3 | — | — |
| 1 | NQ | NQ | NQ | NQ | NQ | — | — | — |
| 2 | NQ | NQ | NQ | NQ | NQ | — | — | — |
| 4 | NQ | NQ | NQ | NQ | NQ | — | — | — |
| 6 | NQ | NQ | NQ | NQ | NQ | — | — | — |
| 8 | NQ | NQ | NQ | NQ | NQ | — | — | — |
| 24 | NQ | NQ | NQ | NQ | NQ | — | — | — |
| $C_{max}$ (ng/mL) | 3.3 | NC | NC | NC | NC | 3.3 | — | — |
| $t_{max}$ (h) | NC | NC | NC | NC | NC | — | — | — |
| $AUC_{last}$ (ng/mL * h) | NC | NC | NC | NC | NC | — | — | — |
| $AUC_{inf}$ (ng/mL * h) | NC | NC | NC | NC | NC | — | — | — |
| % Extrapolation | NC | NC | NC | NC | NC | — | — | — |
| M.R.T. po (h) | NC | NC | NC | NC | NC | — | — | — |

NQ: Not quantifiable. No peak or below limit of quantification (LOQ = 2.5 ng/mL)
NC: Not calculated.

TABLE 4

BT070 Rat PK.

| Time (h) | Animal ID | | | Mean (ng/mL) | SD (ng/mL) | % CV |
|---|---|---|---|---|---|---|
| | A | B | C | | | |
| 0.25 | 6273.9 | 1109.8 | 1684.1 | 3022.6 | 2830.3 | 93.6 |
| 0.5 | 7472.8 | 746.7 | 2546.3 | 3588.6 | 3482.1 | 97.0 |
| 1 | 4382.8 | 725.2 | 1796.5 | 2301.5 | 1880.4 | 81.7 |
| 2 | 2238.3 | 1114.4 | 1215.5 | 1522.8 | 621.7 | 40.8 |
| 4 | 1178.8 | 861.5 | 448.5 | 829.6 | 366.2 | 44.1 |
| 6 | 641.5 | 543.6 | 280.0 | 488.3 | 187.0 | 38.3 |
| 8 | 312.1 | 451.6 | 118.1 | 293.9 | 167.4 | 57.0 |
| 24 | 12.0 | 268.9 | 22.8 | 101.2 | 145.3 | 143.5 |
| $C_{max}$ (ng/mL) | 7472.8 | 1114.4 | 2546.3 | 3711.2 | 3335.4 | 89.9 |
| $t_{max}$ (h) | 0.50 | 2.00 | 0.50 | 1.0 | 0.9 | 86.6 |
| $AUC_{last}$ (ng/mL * h) | 17560.9 | 11798.3 | 7249.5 | 12202.9 | 5167.6 | 42.3 |
| $AUC_{inf}$ (ng/mL * h) | 17616.8 | 19158.4* | 7432.0 | 14735.7 | 6372.0 | 43.2 |
| % Extrapolation | 0.3 | 38.42 | 2.46 | 13.7 | 21.4 | 155.9 |
| CL_F (mL/min/kg) | 9.5 | 8.7* | 22.43 | 13.5 | 7.7 | 57.0 |
| M.R.T. po (h) | 3.1 | 25.0 | 4.2 | 10.8 | 12.3 | 114.4 |

NQ: Not quantifiable. No peak or below limit of quantification (LOQ = 10 ng/mL)
NC: Not calculated.

Tables 5-8, show, respectively, the amount of BT090, BT051, BT070 (the breakdown product of BT051), and BT070 (dosed separately) present in feces of orally-dosed Sprague Dawley rats. Amount assumes that 1 gram of feces equals 1 ml.

TABLE 5

BT090 Amount Excreted Unchanged in Feces Following Oral Administration of a 10 mg/kg dose.

| Time | Animal A 255 g | | | Animal B 239 g | | | Animal C 283 g | | |
|---|---|---|---|---|---|---|---|---|---|
| | Conc.* (μg/mL) | Feces sample (g) | Amount (μg) | Conc. (μg/mL) | Feces sample (g) | Amount (μg) | Conc. (μg/mL) | Feces sample (g) | Amount (μg) |
| 0-4 h | 0.84 | 0.82 | 0.68 | 1.44 | 0.11 | 0.16 | 1.48 | 0.50 | 0.7 |
| 4-8 h | 1109.2 | 1.10 | 1214.6 | 1132.6 | 0.56 | 632.8 | 1.88 | 1.53 | 2.9 |
| 8-24 h | 406.6 | 4.07 | 1653.5 | 1085.3 | 1.34 | 1458.4 | 443.0 | 5.24 | 2323.1 |
| Total (μg) | | | 2868.7 | | | 2091.4 | | | 2326.7 |
| % of dose | | | 112.5 | | | 87.5 | | | 82.2 |

*Concentration corrected for the dilution factor (10-fold for 0-4 h; 50-fold for 4-24 h)

TABLE 6

BT051 Amount Excreted Unchanged in Feces Following Oral Administration of a 10 mg/kg dose.

| Time Interval | Animal A 237 g | | | Animal B 257 g | | | Animal C 243 g | | |
|---|---|---|---|---|---|---|---|---|---|
| | Conc.* (μg/mL) | Feces sample (g) | Amount$^f$ (μg) | Conc.* (μg/mL) | Feces sample (g) | Amount$^f$ (μg) | Conc.* (μg/mL) | Feces sample (g) | Amount$^f$ (μg) |
| 0-4 h | NQ | 0.95 | NC | NC | NS | NC | NQ | 0.60 | NC |
| 4-8 h | 27.1 | 0.97 | 26.3 | NQ | 0.30 | NC | 102.5 | 0.73 | 74.8 |
| 8-24 h | 578.4 | 1.12 | 650.1 | 663.2 | 1.77 | 1175.6 | 321.6 | 3.38 | 1087.7 |
| 24-48 h | 199.3 | 4.69 | 934.4 | 223.1 | 3.83 | 853.7 | 5.8 | 6.40 | 37.0 |
| Total (μg) | | | 1610.7 | | | 2029.4 | | | 1199.6 |
| % of dose | | | 68.0 | | | 79.0 | | | 49.4 |

*Concentration corrected for the dilution factor.
NS: No sample
NC: Not calculated
NQ: Not quantifiable. No peak or below limit of quantification (LOQ = 0.5 g/mL)

TABLE 7

BT070 (breakdown product of BT051) Amount Excreted in Feces Unchanged Following Oral Administration of a 10 mg/kg dose of BT051.

| Time Interval | Animal A 237 g | | | Animal B 257 g | | | Animal C 243 g | | | Animal D 240 g | | |
|---|---|---|---|---|---|---|---|---|---|---|---|---|
| | Conc.* (μg/mL) | Feces sample (g) | Amount<sup>t</sup> (μg)* | Conc.* (μg/mL) | Feces sample (g) | Amount<sup>t</sup> (μg)* | Conc.* (μg/mL) | Feces sample (g) | Amount<sup>t</sup> (μg)* | Conc.* (μg/mL) | Feces sample (g) | Amount<sup>t</sup> (μg)* |
| 0-4 h | NQ | 0.95 | NC | NC | NS | NC | NQ | 0.60 | NC | NQ | 1.09 | NC |
| 4-8 h | NQ | 0.97 | NC | NQ | 0.30 | NC | NQ | 0.73 | NC | NS | NS | NC |
| 8-24 h | 12.7 | 1.12 | 14.3 | 6.0 | 1.77 | 10.6 | 10.3 | 3.38 | 34.8 | 8.7 | 3.58 | 31.2 |
| 24-48 h | 4.08 | 4.69 | 19.1 | 8.1 | 3.83 | 30.8 | 0.6 | 6.40 | 3.7 | 0.8 | 7.27 | 5.7 |
| Total (μg) | | | 33.4 | | | 41.4 | | | 38.5 | | | 36.9 |
| % Parent dose | | | 3.6 | | | 4.1 | | | 4.1 | | | 4.0 |

*Concentration corrected for the dilution factor.
NS: No sample
NC: Not calculated
NQ: Not quantifiable. No peak or below limit of quantification (LOQ = 0.5 g/mL)

TABLE 8

BT070 Amount Excreted Unchanged in Feces Following Oral Administration of a 10 mg/kg dose.

| Time | Animal A 272 g | | | Animal B 280 g | | | Animal C 262 g | | |
|---|---|---|---|---|---|---|---|---|---|
| | Conc.* (μg/mL) | Feces sample (g) | Amount<sup>t</sup> (μg) | Conc.* (μg/mL) | Feces sample (g) | Amount<sup>t</sup> (μg) | Conc.* (μg/mL) | Feces sample (g) | Amount<sup>t</sup> (μg) |
| 0-4 h | NQ | 0.16 | — | 1417.4 | 0.40 | 561.4 | NQ | 1.63 | — |
| 4-8 h | 155322.5 | 1.17 | 181805.0 | NQ | 0.24 | — | 366163.0 | 2.39 | 875239.4 |
| 8-24 h | 333649.7 | 3.09 | 1030677.2 | 314317.5 | 0.80 | 252114.1 | 153005.0 | 6.64 | 1016595.6 |
| Total (μg) | | | 1212482.2 | | | 252675.5 | | | 1891835.1 |
| % of dose | | | 44.6 | | | 9.0 | | | 72.2 |

*Concentration corrected for the 1:9 dilution factor.
NQ: Not quantifiable. No peak or below limit of quantification (LOQ = 1000 ng/mL)

Example 5: Inhibition of FPR1 by Compounds of the Present Technology

This example demonstrates the use of compounds of the present technology for the inhibition of FPR1, as measured by the inhibition of fMLP-induced neutrophil migration.

A. BT051

T84 colorectal cancer cells were grown to confluence on the bottom side of 12 well polycarbonate membrane inserts of a 24 well Transwell® plate. The confluent growth of these epithelial cells results in physiologically-relevant apical (luminal) and basolateral surfaces in the transwells. Freshly isolated and prepared human neutrophils were pretreated in compound (BT051 or cyclosporine A) for 1 hour on ice.

BT051 or cyclosporine A was added to the apical surface of the monolayer. The potent neutrophil chemoattractant, N-formyl-methionyl-leucyl-phenylalanine (fMLP) (100 nM), which activates neutrophil migration via its interaction with the FPR1 protein on neutrophils, was also added to the apical side of the monolayer. The compound-treated neutrophils were then added to the basolateral side and allowed to transmigrate through the monolayer for 2 hours. The number of neutrophils migrated to the apical chamber (due to the fMLP gradient) was then assayed by determination of myeloperoxidase activity (a neutrophil biomarker). Inhibition of transmigration is indicated by lower MPO activity in the apical chamber.

Results. As shown in FIG. 3A, BT051 inhibits fMLP-mediated polymorphonuclear cell (PMN) transmigration/activation. Human PMNs were pretreated with BT051 and added to the "basolateral" side of an epithelial monolayer in a transwell system. fMLP was present on the "apical" side of the transwell as a chemoattractant/neutrophil activator. BT051 blocked transmigration to the apical side and activation of PMNs significantly at 10 uM and 1 uM concentrations, similar to known FPR1 inhibitor cyclosporine A (CsA).

These results show that the compositions of the present technology inhibit FPR1. Accordingly, the compounds are useful in methods comprising the inhibition of FPR1, such as in the treatment of FPR1-mediated diseases such as celiac disease.

B. BT070 and BT090

T84 colorectal cancer cells are grown to confluence on the bottom side of 12 well polycarbonate membrane inserts of a 24 well Transwell® plate. The confluent growth of these epithelial cells results in physiologically-relevant apical (luminal) and basolateral surfaces in the transwells. Freshly isolated and prepared human neutrophils are pretreated in BT070, BT090, or cyclosporine A for 1 hour on ice.

BT070, BT090, or cyclosporine A is added to the apical surface of the monolayer. The potent neutrophil chemoattractant, N-formyl-methionyl-leucyl-phenylalanine (fMLP), which activates neutrophil migration, is also added to the apical side of the monolayer. The compound-treated neutrophils are then added to the basolateral side and allowed to transmigrate through the monolayer for 2 hours. The number of neutrophils migrated to the apical chamber (due to the fMLP gradient) is then assayed by determination of myeloperoxidase activity (a neutrophil biomarker). Inhibition of transmigration is indicated by lower MPO activity in the apical chamber.

Figure 3B:
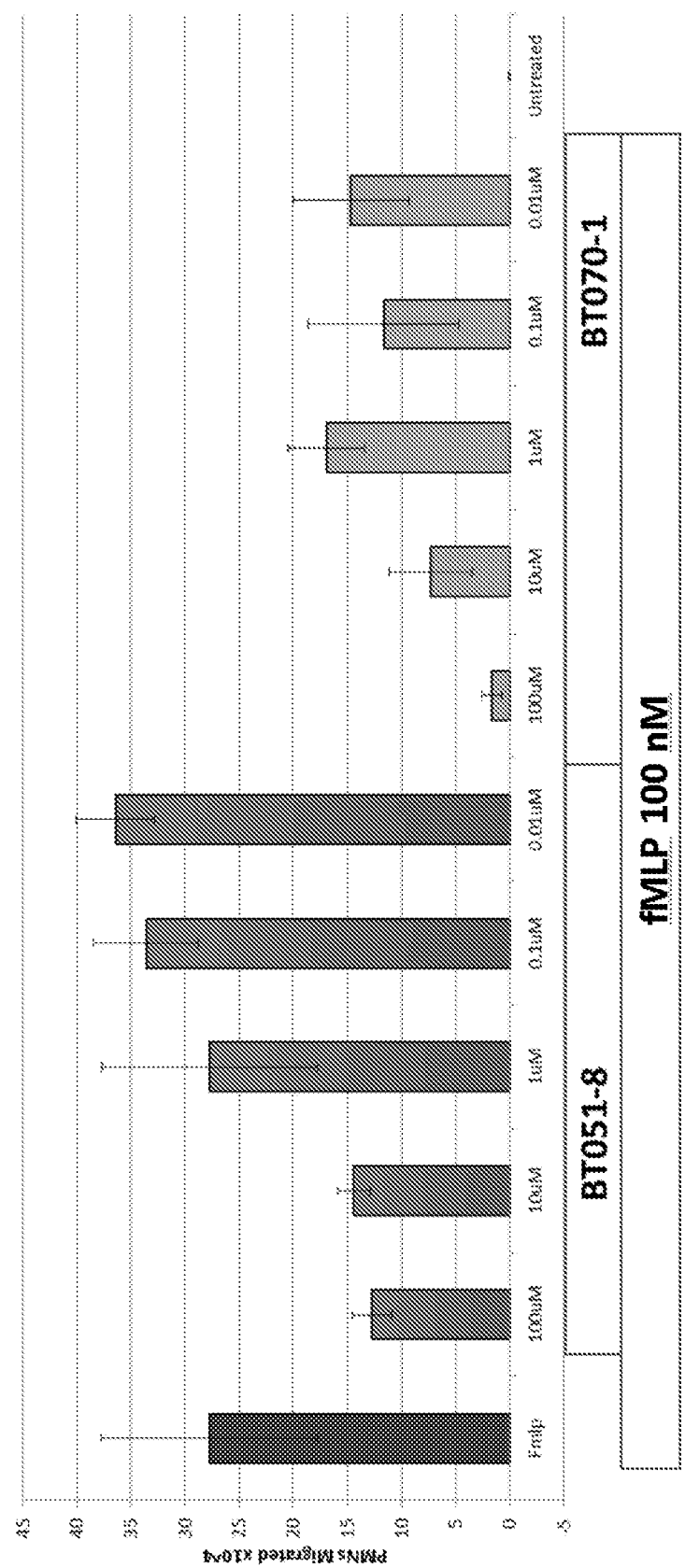

Results. As shown in FIG. 3B, BT070 and BT051 inhibit fMLP-mediated polymorphonuclear cell (PMN) transmigration/activation. It is predicted that and BT090 will also inhibit fMLP-mediated PMN transmigration/activation. BT070 inhibited PMN transmigration/activation by approximately 50%. In this experiment, BT051 inhibited PMN transmigration/activation by 50% at a 10 uM concentration.

These results show (or will show) that the compositions of the present technology inhibit FPR1. Accordingly, the compounds are useful in methods comprising the inhibition of FPR1, such as in the treatment of FPR1-mediated diseases such as celiac disease.

Example 6: Compounds of the Present Technology for the Prevention and Treatment of Colitis This example demonstrates the use of compounds of the present technology for the prevention and treatment of colitis in animal models and human subjects.

Animal Models

Animal models suitable for use in this example include, but are not limited to, animals having colitis, such as those described herein. One of skill in the art will understand that the following description is illustrative and may be applied as appropriate to other animal models.

General. $C_{57}BL/6$ and cnr2-/- mice will be purchased from Jackson laboratories; FVB wt and mdr1a-/- will be purchased from Taconic. Female mice are used at age 6-12 weeks, and genotypes are mixed for at 2-4 weeks prior to experiments to equalize the microbiota. Mice are treated with 3% DSS (molecular weight 36,000-50,000, MP Biomedicals) in the drinking water for 7 days, then placed back on normal water and sacrificed at day 9, which represented peak disease. Samples from mid and distal colon are fixed in 10% formalin, paraffin-embedded, sectioned, and stained for histopathological analysis with hematoxylin and eosin. Each sample is graded semi-quantitatively from 0 to 3 for four criteria: (1) degree of epithelial hyperplasia and goblet cell depletion; (2) leukocyte infiltration in the lamina propria; (3) area of tissue affected; and (4) the presence of markers of severe inflammation such as crypt abscesses, submucosal inflammation, and ulcers. Samples are scored by a trained investigator blinded to sample identity, and mid and distal values are averaged to give colon histopathology score.

Subjects are administered compounds of the present technology according to methods described herein, such as by intrarectal administration. In some embodiments, the compound is administered once daily, once weekly, or once monthly. In some embodiments, compounds are administered multiple times daily, multiple times weekly, or multiple times monthly. Control subjects are administered vehicle alone.

Isolation of lamina propria leukocytes and flow cytometry. Cell suspensions from the lamina propria are prepared as described previously (Buonocore et al., 2010). Intestinal tissue is cut into small pieces, treated with RPMI with 10% FBS and 5 mM EDTA to remove epithelial cells, and then incubated with 100 U/mL Collagenase Type VIII (Sigma-Aldrich) for two 1 hr periods. Cells are then applied to a discontinuous 30/40/75% gradient of Percoll (GE Healthsciences) and harvested from the 40/70% interface. Cells are washed in PBS/0.1% BSA, incubated with anti-Fc receptor (αCD16/32, eBioscience) and stained with Zombie Live/Dead infrared stain (eBioscience) then surface stained with antibodies to CD45, CD11b, Ly6G, and Ly6C or Gr1. Samples are run on a MACSquant Analyzer 10 (Miltenyi Bioscience) and analyzed using Flowjo software Version 10 (Treestar).

Analysis of myeloperoxidase content in mouse samples. Samples are assayed for myeloperoxidase activity as described. Tissue sections of colon are frozen in liquid $N_2$ and stored at −80° C. until use. Sections are put in hexadecyl trimethyl ammonium bromide (HTAB, Sigma) buffer with lysing matrix D (MP Biomedicals) and homogenized with a FastPrep-24 homogenizer at level 6 for 40 s. Samples are combined with ABTS and fluorescence read over 8 min. Slopes are calculated by linear regression using Graphpad Prism, and normalized to protein content for individual samples as measured by Bicinchonic Acid assay (BioRad). For analysis of fecal samples, fecal contents are weighed and HTAB buffer added at a ratio of 10 µL/mg, and calculated slopes are used directly.

Mass spectrometric analysis of $HXA_3$ in colonic mucosa. Mice are administered 5% DSS in their drinking water and sacrificed on day 7. The proximal colon from untreated or DSS-treated mice (9 mice/cohort) is harvested and three intestinal segments pooled. Mucosal scrapings are collected by scraping intestinal surfaces with a rubber policeman in PBS, and $HXA_3$ content is analyzed as previously described (Mumy, K. L. et al., *Infect. Immun.* 76:3614-3627 (2008).

Results. It is expected that intrarectal administration of compounds of the present technology will significantly reduce intestinal pathology and colon shortening induced by DSS as compared to control animals. Analysis of colon histopathology will show that mice treated with the compounds have reduced neutrophil infiltration into the colonic lumen, which will be confirmed by a significant reduction in myeloperoxidase in fecal samples.

Accordingly, it is expected that these results will show that the compounds of the present technology are useful in methods of reducing neutrophil infiltration in vivo, such as in the prevention and treatment of inflammatory condition associated with neutrophil migration, such as colitis.

Human Subjects

Human subjects diagnosed as having or suspected to have colitis or a related disorder and presently displaying one or more symptoms and/or pathologies of colitis or a related disorder, are recruited using selection criteria known and accepted in the art.

Methods of Prevention and Treatment: Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of colitis or related disorders and assessed for reversal of symptoms/pathologies or attenuation of expected symptoms/pathologies using methods known in the art.

Results: It is expected that compounds of the present technology will induce reversal of symptoms and/or pathologies of colitis and related disorders in human subjects. These results will show that compounds of the present technology are useful and effective for the prevention and treatment of such disorders.

Example 7: Compounds of the Present Technology for the Prevention and Treatment of Neutrophil-Mediated Skin Disorders This example demonstrates the use of compounds of the present technology for the prevention and treatment of neutrophil-mediated skin disorders such as dermatitis (eczema), rosacea, seborrheic dermatitis, and psoriasis in animal models and human subjects. One of skill in the art will understand that the example set forth below relating to psoriasis is illustrative of neutrophil-mediated skin disorders, with methods generally applicable to any neutrophil-mediated skin disorder.

Animal Models

Animal models suitable for this example include any accepted psoriasis model, including, but not limited to, models having spontaneous mutations, genetically engineered animals, immunological models, and pharmacological models. Spontaneous mutation models include but are not limited to mice homozygous for the asebia ($Scd1^{ab}/Scd1^{ab}$), chronic proliferative dermatitis ($Sharpin^{cpdm}/Sharpin^{cpdm}$) flaky skin ($Ttc7^{fsn}/Ttc7^{fsn}$) mutations. Genetically engineered models include animals ectopically expressing key regulatory molecules or lacking key regulatory molecules as known in the art. Immunological models include animal subjects subjected to adoptive transfer or related methods as known in the art. Pharmacological models include subjects administered agents that induce psoriasis or psoriasis-related conditions. For example, subjects topically administered imiquimod (IMQ), a toll-like receptor (TLR)-7 and TLR-8 agonist.

One of skill in the art will understand that the following description is illustrative and may be applied as appropriate to other animal models.

Materials. Imiquimod (IMQ, 5% cream, Beselna®) is purchased from Mochida Pharmaceutical (Tokyo, Japan). Betamethasone butyrate propionate (0.05% ointment, Antebate®) is purchased from Torii Phar maceutical (Tokyo, Japan). Real-time PCR probes and related agents is purchased from Applied Biosystems (Massachusetts, USA).

Animals. Female BALB/c mice and male CB-17 scid mice aged 7-12 weeks old are housed under specific pathogen-free conditions at a room temperature of 23±3° C. and air humidity of 55±15% in a 12-hour light/dark cycle environment, and provided with food and water ad libitum.

Induction of skin inflammation. IMQ 5% cream is applied on inner and/or outer sides of the left ear skin once daily. The dose of IMQ is either 250 ug on outer side, 500 ug on outer side, or 250 ug on both inner and outer sides of the ear. Betamethasone ointment or relevant ointment base is applied twice daily on to the left ear, at a volume of 5 uL to both the inner and/or outer sides. Thickness of the left ear is measured as a quantitative index of skin inflammation utilizing a thickness gauge (IDA-112M, Mitutoyo, Kawasaki, Japan) once daily before the application of IMQ. Control subjects are administered vehicle alone.

For methods of prevention, subjects are pre-treated with compounds of the present technology by topical application for a pre-determined period prior to IMQ exposure.

For methods of treatment, subjects are topically administered compounds of the present technology for a pre-determined period following confirmation of IMQ-induced inflammation using methods known in the art.

Subjects are euthanized by carbon dioxide gas, and the left ear harvested after examination of gross morphology for erythema and scaling. A portion of the harvested tissue is sliced, fixed with buffered 10% formalin solution, and processed for preparation of histological paraffin sections. The sections are stained with hematoxyline and eosin, and subjected to light microscopic examination. The remaining tissue is stored at −80° C. for mRNA analysis by real time PCR.

Real time PCR assays. Total RNA samples in the ear tissues are obtained with RNeasy® Lipid Tissue Mini Kit (QIAGEN, Venlo, the Netherlands), following the manufacturer's instructions. The level of transcripts coding cytokines of interest in the present study are measured by the TaqMan Gene Expression Assays using the RNA-to-Ct™ 1-Step Kit.

Illustrative targets include but are not limited to IFN-γ, IL-13, IL-17, IL-22, IL-23, TNF-α, and IL-1β. Target transcript levels are normalized to GAPDH transcript levels.

Statistical Analysis. Values of ear thickness are shown as increases from the pre-treatment values measured at Day 1 and expressed as mean±standard deviation (S.D.). Statistical significance is analyzed by F-test followed by Aspin-Welch's t-test and Bartlett's test followed by Dunnett's test or Steel test in ear thicknesses, and by Bartlett's test followed by Tukey's test or Steel-Dwass test in mRNA transcript levels. A p value of less than 0.05 was considered statistically significant.

Results. It is predicted that administration of compounds of the present technology will prevent or reduce IMQ-induced inflammation as measured by tissue thickness, inflammatory gene expression, and dermal neutrophil infiltration. These results will show that compounds of the present technology are useful in the prevention and treatment of conditions associated with inflammation and dermal neutrophil infiltration, including but not limited to dermatitis (eczema), rosacea, seborrheic dermatitis, and psoriasis.

Human Subjects

Human subjects diagnosed as having or suspected to have a neutrophil-mediated skin disorder, such as dermatitis (eczema), rosacea, seborrheic dermatitis, or psoriasis, and presently displaying one or more symptoms and/or pathologies of the disorder, are recruited using selection criteria known and accepted in the art.

Methods of Prevention and Treatment. Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of neutrophil-mediated skin disorder and assessed for reversal of symptoms/pathologies or attenuation of expected symptoms/pathologies using methods known in the art. For example, subjects are administered compounds of the present technology prior to or subsequent to the development of a neutrophil-mediated skin disorder or symptoms thereof. Subjects are then assessed for prevention, reversal, or attenuation of the disorder or symptom using methods known in the art.

Results. It is expected that compounds of the present technology will induce reversal of symptoms and/or pathologies of neutrophil-mediated skin disorders, such as dermatitis (eczema), rosacea, seborrheic dermatitis, and psoriasis. These results will show that compounds of the present technology are useful and effective for the prevention and treatment of neutrophil-mediated skin disorders in human subjects.

Example 8: Compounds of the Present Technology for the Prevention and Treatment of Celiac Disease This example demonstrates the use of compounds of the present technology for the prevention and treatment of celiac disease. One of skill in the art will understand that the example set forth below is illustrative of gluten intolerance disorders generally, with methods generally applicable to celiac disease and related disorders.
Animal Models
Animal models suitable for this example include any accepted celiac model, including, but not limited to, spontaneous models such as dog and monkey models known in the art, induced models such as germ-free Wistar AVN rats administered gliadin immediately after birth, and transgenic models such as animals overexpressing IL-15. One of skill in the art will understand that the following description is illustrative and may be applied as appropriate to other animal models.

General. Animal models are selected and maintained according to relevant standards known in the art. Subjects are administered compounds of the present technology according to methods described herein, such as by oral administration. In some embodiments, the compound is administered once daily, once weekly, or once monthly. In some embodiments, compounds are administered multiple times daily, multiple times weekly, or multiple times monthly. Control subjects are administered vehicle alone.

For methods of prevention, subjects are administered compounds of the present technology prior to or subsequent to the development of symptoms and/or pathologies of celiac disease or related disorders and assessed for reversal of symptoms/pathologies or attenuation of expected symptoms/pathologies using methods known in the art.

Results: It is expected that compounds of the present technology will induce reversal of symptoms and/or pathologies of celiac disease and related disorders in animal models. These results will show that compounds of the present technology are useful and effective for the prevention and treatment of celiac disease and related disorders.
Human Subjects
Human subjects diagnosed as having or suspected to have celiac disease or a related disorder and presently displaying one or more symptoms and/or pathologies of celiac disease or a related disorder, are recruited using selection criteria known and accepted in the art.

Methods of Prevention and Treatment: Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

For methods of prevention, subjects are administered compounds of the present technology prior to or subsequent to the development of symptoms and/or pathologies of celiac disease or related disorders and assessed for reversal of symptoms/pathologies or attenuation of expected symptoms/pathologies using methods known in the art.

Results: It is expected that compounds of the present technology will induce reversal of symptoms and/or pathologies of celiac disease and related disorders in human subjects. These results will show that compounds of the present technology are useful and effective for the prevention and treatment of celiac disease and related disorders.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

Each and every publication and patent mentioned in the above specification is herein incorporated by reference in its entirety for all purposes. Various modifications and variations of the described methods and system of the present technology will be apparent to those skilled in the art without departing from the scope and spirit of the present technology. Although the present technology has been described in connection with specific embodiments, the present technology as claimed should not be unduly limited to such specific embodiments. Indeed, various modifications of the described modes for carrying out the present technology which are obvious to those skilled in the art and in fields related thereto are intended to be within the scope of the following claims.

What is claimed is:

1. A compound having the structure of Formula I,

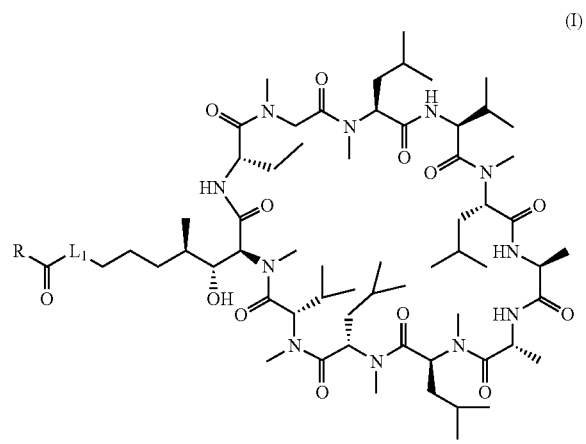

a stereoisomer thereof, or a pharmaceutically acceptable salt of any of the foregoing;
wherein
$L_1$ is a $C_1$ to $C_4$ alkyl group optionally substituted with one or more F;
R is a PEG having from 40 to 50 ethylene oxide units, wherein the PEG comprises a linker group, $L_2$; and
$L_2$ is a $C_{1-6}$ unsubstituted heteroalkylene having one or two nitrogen atoms.

2. The compound of claim 1, wherein R is selected from —NH $(CH_2)_{2-6}$ $(CH_2CH_2O)_{42-46}$—O $(CH_2)_{0-5}CH_3$.

3. The compound of claim 1, wherein R is $CH_3O$—$(CH_2CH_2O)_{44}$—$CH_2CH_2CH_2NH$—.

4. The compound of claim 1, wherein Li is an ethylene group or a propylene group.

5. The compound of claim 3 having the structure of Formula IA, a stereoisomer thereof, or a pharmaceutically acceptable salt of any of the foregoing:

(IA)

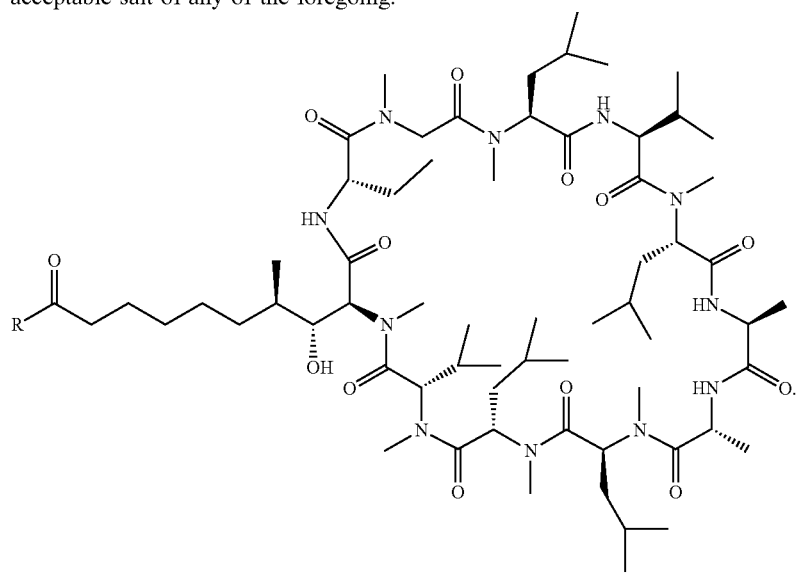

6. A pharmaceutical composition comprising the compound of claim 1 and a pharmaceutically acceptable carrier.

7. A method for treating a disease associated with neutrophil-mediated inflammation in a target tissue of a mammalian subject in need thereof, comprising administering to the subject a therapeutically effective amount of a compound of formula I:

(I)

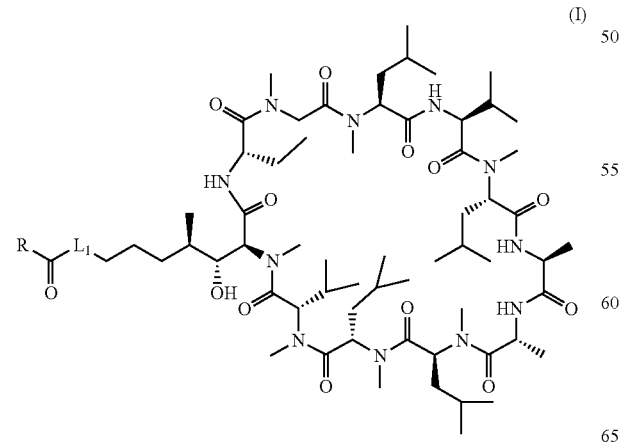

a stereoisomer thereof, or a pharmaceutically acceptable salt of any of the foregoing;
wherein
$L_1$ is a $C_1$ to $C_4$ alkyl group optionally substituted with one or more F;
R is a PEG having from 40 to 50 ethylene oxide units, wherein the PEG comprises a linker group, $L_2$; and
$L_2$ is a $C_{1-6}$ unsubstituted heteroalkylene having one or two nitrogen atoms.

8. The method of claim 7, wherein R is $CH_3O$—$(CH_2CH_2O)_{44}$—$CH_2CH_2CH_2NH$—.

9. The method of claim 7, wherein Li is an ethylene group or a propylene group.

10. The method of claim 8, wherein the compound of formula I has the structure of Formula IA or a pharmaceutically acceptable salt thereof:

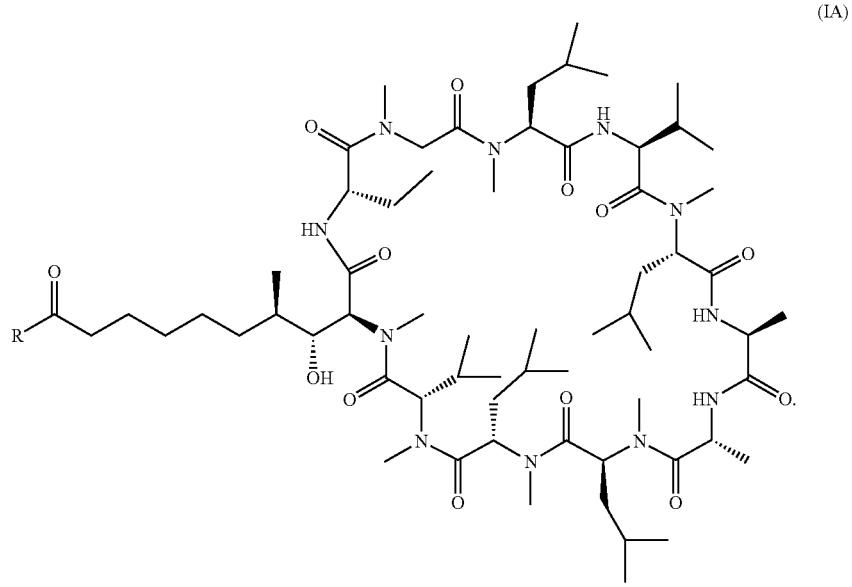

(IA)

11. The method of claim 7, wherein the compound is formulated as a pharmaceutical composition comprising the compound and a pharmaceutically acceptable carrier.

12. The method of claim 7, wherein the disease is selected from the group consisting of intestinal disease, colitis, inflammatory lung disease, inflammatory skin disease, ocular disease, urogenital disease, and sexually transmitted diseases.

13. The method of claim 12, wherein:
the intestinal disease is selected from the group consisting of proctitis, orchitis, Crohn's disease, and celiac disease;
the colitis is selected from the group consisting of ulcerative colitis, also known as colitis ulcerosa, infectious/non-infectious enterocolitis, and inflammatory bowel disease (IBD);
the inflammatory lung disease is selected from the group consisting of pneumococcal infection, asthma, chronic obstructive pulmonary disease (COPD), and pulmonary fibrosis;
the inflammatory skin disease is selected from the group consisting of dermatitis (eczema), rosacea, seborrheic dermatitis, and psoriasis;
the ocular disease is selected from the group consisting of uveitis, retinitis, keratitis, and macular degeneration;
the urogenital disease comprises a urinary tract infection; and
the sexually transmitted disease is selected from the group consisting of pelvic inflammatory disease, gonorrhea infection, chlamydia infection, herpes, and urethritis.

14. The method of claim 7, wherein the administering step is selected from the group consisting of topical administration and administration at a luminal surface of the target tissue.

15. The method of claim 7, wherein the inflammation is non-infectious inflammation or infectious inflammation.

16. The method of claim 7, wherein the method further comprises:
administering to the subject a therapeutically effective amount of one or more second compound that inhibits one or more of multidrug resistance protein 2 (MRP2) and hepoxilin A3 ($HXA_3$) synthase, wherein the therapeutic amount of the second compound reduces migration of neutrophils into the target tissue; and/or
administering to the subject a therapeutically effective amount of one or more compounds that increases multidrug resistance protein 1 (MRP1), wherein the therapeutic amount of the one or more compounds that increases MRP1 reduces migration of neutrophils into the target tissue; and/or
administering to the subject a therapeutically effective amount of one or more compounds that increases one or more N-acylethanolamines (NAEs), wherein the therapeutic amount of the one or more compounds that increases NAEs reduces migration of neutrophils into the target tissue.

17. The method of claim 7, wherein the inflammation is associated with:
Crohn's disease and the treatment further comprises administering one or more mesalamine products, corticosteroid formulations, ileal-release budesonide, glucocorticosteroids/EEN immunomodulatives, anti-tumor necrosis factor (TNF) drugs, anti-alpha-4 beta-7 integrin antibody vedolizumab, ABT-494, and filgotinib; and/or ulcerative colitis and the treatment further comprises administering one or more of 5-aminosalycylates, mesalamine, corticosteroids, multimatrix budesonide, azathioprine, 6-mercaptopurine, anti-TNF drugs, vedolizumab, tofacitinib, ABT-494, and filgotinib.

18. The method of claim 7, further comprising administering one or more antibiotic and/or anti-inflammatory agents selected from the group consisting of: Dalbavancin, Oritavancin, Cubicin, Tedizolid, Ceftobiprole, Ceftobiprole, Ceftolozane-tazobactam, mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents, non-steroidal agents, immunosuppresant agents, and cytokine synthesis inhibitors, tetracycline, minocycline, and doxycycline, or any combination thereof.

19. The method of claim 7 further comprising administering one or more antibodies selected from the group consisting of: antibodies targeting *Clostridium difficile* toxins, antibodies targeting tumor necrosis factor (TNF), antibodies targeting interleukins, and antibodies targeting metalloproteinase-9.

20. The method of claim 7, wherein the compound of Formula I reduces migration of neutrophils into the target tissue as compared to untreated control tissue.

21. The method of claim 17, wherein: the glucocorticosteroids/EEN immunomodulatives are selected from one or more of azathioprine, 6-mercaptopurine, and methotrexate; and the anti-TNF drugs are selected from one or more of infliximab, adalimumab, golimumab, and certolizumab pegol.

22. The method of claim 18, wherein: the steroidal agents comprise a corticosteroid; the non-steroidal agents are selected from one or more of COX inhibitors, LOX inhibitors, and p38 kinase inhibitors; and the immunosuppressant agents comprise cyclosporine.

23. The method of claim 22, wherein the corticosteroid is selected from one or more of hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, and triamcinolone.

\* \* \* \* \*

UNITED STATES PATENT AND TRADEMARK OFFICE
CERTIFICATE OF CORRECTION

PATENT NO. : 12,252,556 B2
APPLICATION NO. : 17/269614
DATED : March 18, 2025
INVENTOR(S) : Chris Murphy, Ronald Farquhar and Roland E. Dolle It is certified that error appears in the above-identified patent and that said Letters Patent is hereby corrected as shown below:

In the Claims

Column 63, Claim 18, Lines 9-10, "Ceftobiprole, Ceftobiprole, Ceftolozane-tazobactam," should read -- Ceftobiprole, Ceftolozane-tazobactam, --.

Column 63, Claim 18, Line 15, "immunosuppresant agents" should read -- immunosuppressant agents --.

Signed and Sealed this
Twenty-second Day of April, 2025

Coke Morgan Stewart
*Acting Director of the United States Patent and Trademark Office*